(12) United States Patent
Robertson et al.

(10) Patent No.: US 8,957,012 B2
(45) Date of Patent: *Feb. 17, 2015

(54) GAMMA SECRETASE INHIBITOR FOR TREATMENT OF HERPESVIRUS INFECTION

(75) Inventors: Erle S. Robertson, Wynnewood, PA (US); Ke Lan, Upper Darby, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/357,452

(22) Filed: Jan. 24, 2012

(65) Prior Publication Data

US 2012/0183508 A1    Jul. 19, 2012

Related U.S. Application Data

(63) Continuation of application No. 11/822,419, filed on Jul. 5, 2007, now Pat. No. 8,110,557.

(60) Provisional application No. 60/818,306, filed on Jul. 5, 2006.

(51) Int. Cl.

| | |
|---|---|
| *A61K 35/76* | (2006.01) |
| *A61K 38/00* | (2006.01) |
| *A61K 31/195* | (2006.01) |
| *A61K 31/216* | (2006.01) |
| *A61K 31/7105* | (2006.01) |
| *A61K 31/711* | (2006.01) |
| *C12Q 1/68* | (2006.01) |

(52) U.S. Cl.
CPC ............. *A61K 31/195* (2013.01); *A61K 31/216* (2013.01); *A61K 31/7105* (2013.01); *A61K 31/711* (2013.01)
USPC ............... 514/1; 514/44 A; 514/4.2; 424/93.6

(58) Field of Classification Search
None
See application file for complete search history.

(56) References Cited

U.S. PATENT DOCUMENTS

| | | | | |
|---|---|---|---|---|
| 6,756,203 | B2 * | 6/2004 | Kieff et al. | 435/6.13 |
| 2003/0181380 | A1 * | 9/2003 | Pear et al. | 514/12 |
| 2004/0229816 | A1 * | 11/2004 | Paris et al. | 514/18 |

OTHER PUBLICATIONS

Grunweller et al Nucleic Acids Research vol. 31:3185-3193, 2003.*
Lan et al. "Induction of Kaposi's Sarcoma-Associated Herpesvirus Latency-Associated Nuclear Antigen by the Lytic Transactivator RTA: a Novel Mechanism for Establishment of Latency J." Virol. 79:7453-7465, Jun. 15, 2005.
Lan et al. Kaposi's Sarcoma-Associated Herpesvirus Reactivation Is Regulated by Interaction of Latency-Associated Nuclear Antigen with Recombination Signal Sequence-Binding Protein J{kappa}, the Major Downstream Effector of the Notch Signaling Pathway J. Virol. 79:3468-3478. Mar. 15, 2005.
Lan et al. Kaposi's Sarcoma-Associated Herpesvirus-Encoded Latency-Associated Nuclear Antigen Inhibits Lytic Replication by Targeting RTA: a Potential Mechanism for Virus-Mediated Control of Latency J. Virol. 78:6585-6594. Jun. 15, 2004.
Sefton MV. "Implantable Pumps. Critical Reviews in Biomedical Engineering"; 14:201-240. (1987).
Buchwald et al. "Long-term, continuous intravenous heparin administration by an implantable infusion pump in ambulatory patients with recurrent venous thrombosis" Surgery 88:507 (1980).
Saudek et al. "A Preliminary Trial of the Programmable Implantable Medication System for Insulin Delivery" N. Engl. J. Med. 321:574, (1989).
Goodson. "In Medical Applications of controlled Release" supra, vol. 2, pp. 115-138 (1984).
Langer R. "New methods of drug delivery", Science; 249: 1527-1533, (1990).
Nielsen et al. "Synthesis of 2'-O, 3'-C-Linked Bicyclic Nucleosides and Bicyclic Oligonucleotides" J. Chem. Soc., Perkin Trans. 1, 3423-3433, (1997).
Koshkin. "Novel convenient syntheses of LNA [2.2.1]bicyclo nucleosides" Tetrahedron Letters, vol. 39, No. 24, , pp. 4381-4384. Jun. 11, 1998.
Singh and Wengel. "Universality of LNA-Mediated High-Affinity Nucleic Acid Recognition" Chem. Commun., 1247-1248, (1998).
Singh et al. "LNA (Locked Nucleic Acids): Synthesis and High Affinity Nucleic Acid Recognition" Chem. Commun., 455-456, (1998).
Katre et al. "Chemical modification of recombinant interleukin 2 by polyethylene glycol increases its potency in the murine Meth A sarcoma model" Proc. Natl. Acad. Sci. USA vol. 84, pp. 1487-1491, Biochemistry, Mar. 1987.
Russo et al. "Nucleotide sequence of the Kaposi sarcoma-associated herpesvirus (HHV8)"Proc. Natl. Acad. Sci. USA vol. 93, pp. 14862-14867 Microbiology, Dec. 1996.
Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.
Aster et al. Activate Transcription the Ability to Associate with RBP-J k and k or Nuclear Localization Sequences Retain Either the Primary Binding Site for RBP-J Oncogenic Forms of NOTCH1 Lacking Cell Biology and Metabolism: J. Biol. Chem. 272:11336-11343, (1997).

* cited by examiner

*Primary Examiner* — Sean McGarry
(74) *Attorney, Agent, or Firm* — Mark S. Cohen; Pearl Cohen Zedek Latzer Baratz LLP

(57) ABSTRACT

This invention relates to methods and compositions for the treatment of malignancies associated with gamma-herpesvirus infection. Specifically, the invention relates to the use of gamma-secretase inhibitors to prevent the production of intracellular Notch1 thereby arresting the growth of the infected cells.

15 Claims, 21 Drawing Sheets

SEQUENCE LISTING

<160> NUMBER OF SEQ ID NOS: 9

<210> SEQ ID NO 1
<211> LENGTH: 20
<212> TYPE: DNA
<213> ORGANISM: Homo sapiens

<400> SEQUENCE: 1
ccttggtgcg tttaacaaca                                        20

<210> SEQ ID NO 2
<211> LENGTH: 20
<212> TYPE: DNA
<213> ORGANISM: Homo sapiens

<400> SEQUENCE: 2
ttatgtaacg cggaactcca                                        20

<210> SEQ ID NO 3
<211> LENGTH: 23
<212> TYPE: DNA
<213> ORGANISM: Homo sapiens

<400> SEQUENCE: 3
gatcatttcc gtgggaagac gat                                    23

<210> SEQ ID NO 4
<211> LENGTH: 20
<212> TYPE: DNA
<213> ORGANISM: Homo sapiens

<400> SEQUENCE: 4
gggcttcaaa gtgtctgagg                                        20

<210> SEQ ID NO 5
<211> LENGTH: 20
<212> TYPE: DNA
<213> ORGANISM: Homo sapiens

<400> SEQUENCE: 5
cggaacttct tggtctccag                                        20

<210> SEQ ID NO 6
<211> LENGTH: 20
<212> TYPE: DNA
<213> ORGANISM: Homo sapiens

<400> SEQUENCE: 6
tatccaggaa gcggtctcat                                        20

<210> SEQ ID NO 7
<211> LENGTH: 20
<212> TYPE: DNA

```
<213> ORGANISM: Homo sapiens

<400> SEQUENCE: 7
gggttaaagg ggatgatgct                                                   20

<210> SEQ ID NO 8
<211> LENGTH: 21
<212> TYPE: DNA
<213> ORGANISM: Homo sapiens

<400> SEQUENCE: 8
gctcgtcgtc gacaacggct c                                                 21

<210> SEQ ID NO 9
<211> LENGTH: 25
<212> TYPE: DNA
<213> ORGANISM: Homo sapiens

<400> SEQUENCE: 9
caaacatgat ctgggtcatc ttctc                                             25
```

GAMMA SECRETASE INHIBITOR FOR TREATMENT OF HERPESVIRUS INFECTION

CROSS REFERENCE TO RELATED APPLICATIONS

This application is a continuation of U.S. patent application Ser. No. 11/822,419, filed on Jul. 5, 2007, now U.S. Pat. No. 8,110,557 which claims benefit of U.S. Provisional Application Ser. No. 60/818,306 filed on Jul. 5, 2006, each of which is hereby incorporated by reference in its entirety.

GOVERNMENT INTEREST

This invention was made with government support under grant number(s) CA072510, CA091792, and DE001436 awarded by National Institute of Health. The government has certain rights in the invention.

FIELD OF INVENTION

This invention is directed to methods and compositions for the treatment of malignancies associated with γ-herpesvirus infection. Specifically, the invention relates to the use of γ-secretase inhibitors to prevent the production of intracellular Notch1 thereby arresting growth of the infected cells.

BACKGROUND OF THE INVENTION

Kaposi's sarcoma-associated herpesvirus (KSHV) is Gamma herpesvirus associated with a number of human malignancies which includes Kaposi's sarcoma (KS), primary effusion lymphoma (PEL) and multicentric Castleman's disease (MCD). Similar to other herpesviruses, KSHV is a large double stranded DNA virus which displays two alternate genetic life cycle programs upon infection of host cells (35)-In latent infection, gene expression is limited to a small subset of viral latent genes and includes the latency associated nuclear antigen (LANA) encoded by ORF73, viral cyclin (v-cyclin) encoded by ORF72, viral Fas-associated death domain (FADD) interleukin-1L-converting enzyme (FLICE) inhibitory protein (v-FLIP) encoded by ORF71, viral interferon (IFN) regulatory factors (vIRFs) encoded by K10 and Kaposin encoded by K12. During latency the viral episome is maintained through successive generations but no viral progeny are produced. In contrast, lytic replication leads to extensive viral gene expression, virion production, and death of the infected cell. Latently infected cells can be induced to enter the lytic cycle under specific physiological conditions. Thus, the pool of latently infected cells represents a reservoir of viral persistence from which infectious virus can be later reactivated with production of viral progeny which can spread to new target cells.

To date, it is widely accepted that latent infection by the virus plays a central role in viral pathogenesis with the expression of select genes responsible for targeting and controlling selective cellular pathways. Occasionally, lytic reactivation of the virus may be critical as expression of viral cytokine homologues during this phase may function as paracrine factors in stimulating cell growth and proliferation. The reduced gene expression pattern of latency minimizes the number of viral epitopes that are presented by infected cells to cytotoxic T lymphocytes (CTLs) and so contributes to the ability of the virus to escape immune surveillance and establishment of persistent infection (8, 9). In addition, a number of studies have shown that the genes expressed during latency play a major role in tumorigenesis of KSHV-associated cancers.

SUMMARY OF THE INVENTION

In one embodiment, the invention provides a method for treating a virus-induced lymphoproliferative disease in a subject, comprising the step of administering to said subject a therapeutically effective amount of γ-secretase inhibitor, wherein said γ-secretase inhibitor prevents accumulation of intracellular Notch1 (ICN), and arrests infected host cells in the G1 phase thereby inhibits the proliferation of lymphoma.

In another embodiment, the invention provides a method of inhibiting or suppressing production of intracellular Notch1 (ICN) resulting from viral transfection, comprising contacting the transfected host cell with an effective amount of a γ-secretase inhibitor, wherein said γ-secretase inhibitor arrests growth of infected host at the G1 phase.

In one embodiment, the invention provides a composition for the treatment of a malignancy associated with a viral transfection, comprising: a therapeutically effective amount of a γ-secretase inhibitor, a pharmaceutically acceptable carrier, excipient, flow agent, processing aid, diluent or a combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
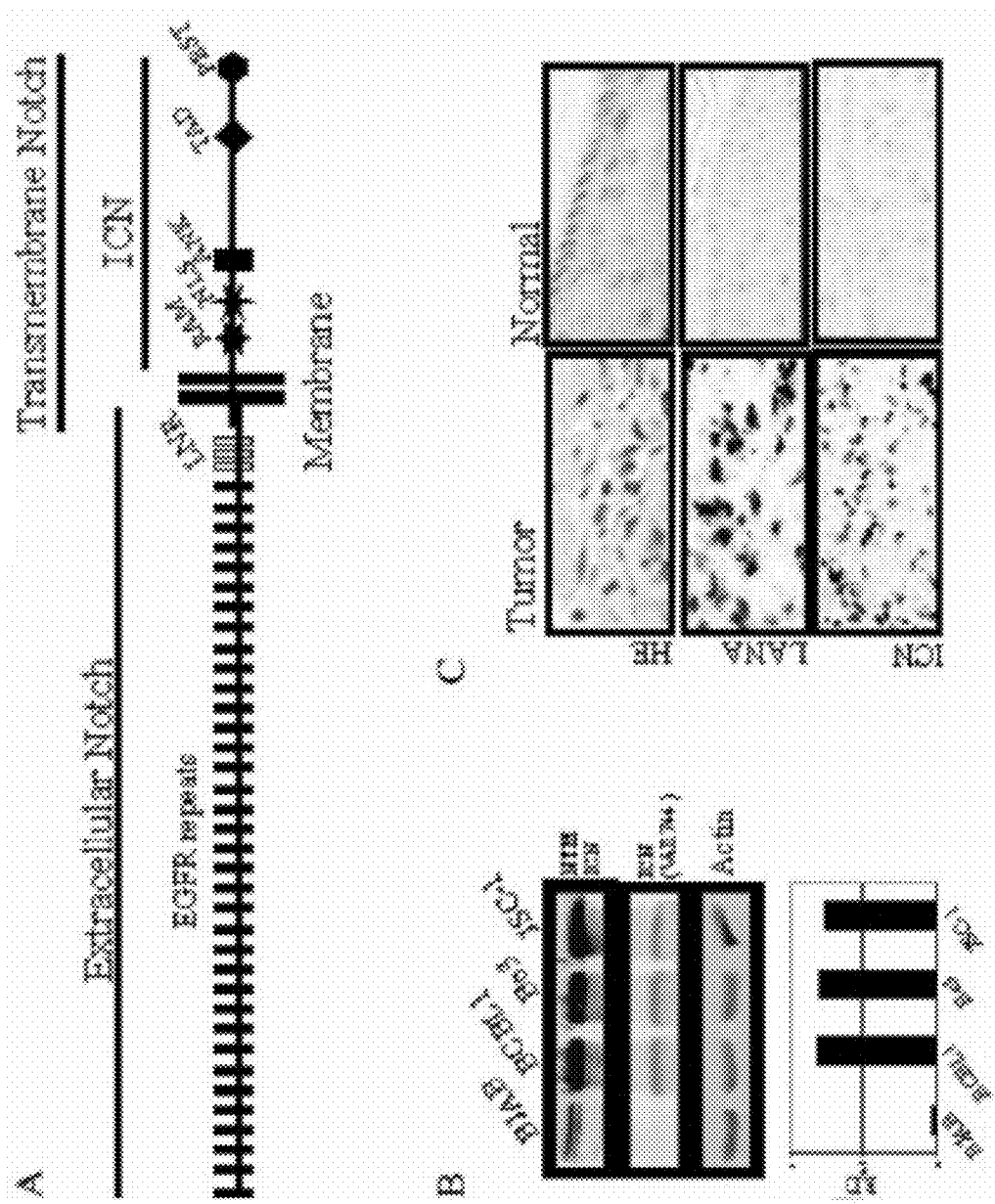
FIG. 1. shows Notch ICN is accumulated in KSHV-infected cells. (A) Scheme showing the Notch1 protein. Notch receptor is heterodimeric transmembrane proteins consisting of an extracellular ligand-binding domain, transmembrane domain, and intracellular domain. The intracellular domain contains a RAM domain, ankyrin repeats, nuclear localization signal, transcriptional activation domain (TAD), and a PEST sequence. The extracellular domain contains multiple EGF-like repeats and LIN12/Notch repeats (LNR). (B) Western blot showing ICN levels in different cells. Cell lysate of BJAB, BCBL1, BC3, and JSC1 was separated on 8% SDS-PAGE gel, transferred to NC membrane, and then blotted with anti-Notch rabbit serum. This anti-serum recognizes the uncleaved transmembrane subunit NTM (upper band) and its intracellular cleavage product ICN (bottom band), respectively. Same samples were also detected with Val1744 antibody which specifically recognizes ICN. The loading amount of lysates was normalized by Bradford assay. Quantification of relative density for ICN from each cell is also shown. (C) Notch1 ICN up-regulation in Kaposi's sarcoma. Kaposi's sarcoma tissue specimens from 3 patients were analyzed for LANA and Notch1 ICN expression by immunohistochemistry. A representative sample shows a strong correlation between LANA expression and ICN expression. Tumor cell staining is presented in the left panel, and the right panel is the adjacent normal tissue staining. The images on the top are HE staining. Magnification, ×40.

This invention relates in one embodiment to methods and compositions for the treatment of malignancies associated with γ-herpesvirus infection. Specifically, the invention relates to the use of γ-secretase inhibitors to prevent the production of intracellular Notch1 thereby arresting the growth of the infected cells.

In one embodiment KSHV LANA, a predominant viral protein during latency, enhances the stability of intracellular activated Notch1 (ICN) molecule in KSHV infected primary effusion lymphoma cells. In another embodiment, the elevation of ICN results in increased proliferation of these tumor cells. In another embodiment, gamma secretase inhibitor that can specifically inhibit the production of ICN, slows down the proliferation of lymphoma tumor cells and cause apoptosis and necrosis of these tumor cells in vitro and in vivo.

KSHV is able to establish two distinct modes of infection: latent and lytic replication. Latency is established soon after primary lytic infection and is characterized in one embodiment by the persistence of the viral genome in the cell nucleus and expression of a small subset of viral genes. Lytic reactivation of latent virus involves the sequential activation of immediate-early, early and late viral genes. In KSHV, this gene expression cascade is initiated in one embodiment, by immediate-early viral transactivator RTA. In one embodiment, ectopic expression of RTA in latently infected B cells is sufficient to reactivate the latent virus and initiate replication. In another embodiment, long-term infection in the host contributes to viral pathogenesis, therefore, maintenance of latent state is a critical component of the virus life cycle.

In one embodiment, lytic reactivation is mediated at the level of the viral genome by the γ-herepesvirus-encoded transcription factor RTA. In another embodiment, overexpression of the RTA gene is sufficient to trigger lytic replication in latently infected B-cell lines. In one embodiment, RTA protein autoactivates the RTA promoter.

In one embodiment, RTA is activated by chemical inducers such as TPA and sodium butyrate. In another embodiment, hypoxia induces lytic replication through up-regulating RTA. During lytic reactivation RTA auto-activates its own promoter, and by using this positive feed back loop, RTA is able to successfully drive lytic replication to completion. In another embodiment RTA is down-regulated by NF-κB and KSHV LANA which is critical for latency control. In another embodiment, RTA activates lytic reactivation through functional interaction with RBP-Jκ. Another γ-herpesvirus EBV, EBNAs modulate gene expression by targeting RBP-Jκ. In another embodiment, LANA down-regulates RTA transcription by binding to RBP-Jκ which serves as a signal transducer, transmitting a series of finely tuned negative or positive regulatory signals to the virus thereby stringently regulate the viral life cycle. Since RBP-Jκ is the major downstream effector of Notch signaling pathway, this demonstrates that in one embodiment, viral proteins replace the function of Notch ICN to modulate specific viral and cellular gene transcription.

In one embodiment, LANA as used herein refers to latency associated nuclear antigen (LANA). In one embodiment, LANA refers to a trans-acting factor that supports episome persistence of gamma-herpesvirus DNA. In another embodiment, LANA acts on a cis-acting element present in a defined region of KSHV DNA to mediate the efficient persistence of episomal DNA in infected host cells. In one embodiment, KSHV DNA recruits a substantial fraction of the LANA molecules in the cell and tethers KSHV episomes to the infected cell's chromosomes during mitosis. Complexing KSHV DNA to chromosomes ensures in another embodiment, an efficient distribution of episomes to progeny cells and the inclusion of KSHV DNA in newly formed nuclei. In another embodiment, LANA binds to the p53 and pRb tumor suppressor proteins as well as glycogen synthase kinase 3β. It can function as a transcriptional activator of its own viral and cellular gene promoters, changing various signaling events. In one embodiment, LANA activates mature B cells in the absence of antigen stimulation, predisposing the infected subject to the development of lymphoproliferative disease.

In one embodiment, RTA is activated by chemical inducers such as TPA and sodium butyrate. In another embodiment, hypoxia induces lytic replication through up-regulation of RTA. During lytic reactivation RTA auto-activates its own promoter, and by using this positive feed back loop, RTA is able to successfully drive lytic replication to completion. In another embodiment RTA is down-regulated by NF-κB and KSHV LANA which is critical for latency control. In another embodiment, RTA activates lytic reactivation through functional interaction with RBP-Jκ. Another γ-herpesvirus EBV, EBNAs modulate gene expression by targeting RBP-Jκ. In another embodiment, LANA down-regulates RTA transcription by binding to RBP-Jκ which serves as a signal transducer, transmitting a series of finely tuned negative or positive regulatory signals to the virus thereby stringently regulate the viral life cycle. Since RBP-Jκ is the major downstream effector of Notch signaling pathway, this demonstrates that in one embodiment, viral proteins replace the function of Notch ICN to modulate specific viral and cellular gene transcription. In one embodiment, Notch signaling pathway plays a critical role in the development of different tissues and cell types, through diverse effects on differentiation, survival, or proliferation or their combination, which are highly dependent on signal strength and the cellular context. In one embodiment, ligand binding triggers a series of protease-based cleavage events which lead to ICN production from the full-length Notch receptor. In another embodiment, ICN is then translocated into nucleus and binds to its major downstream target RBP-Jκ to regulate gene transcription. In one embodiment, the expression level of ICN in KSHV latently infected B lymphocytes is aberrantly high compared to that in KSHV-negative B lymphocytes. In another embodiment, ICN level is greatly elevated in KS tissue, indicating that the Notch pathway acts in one embodiment, in an RBP-Jκ independent manner.

In one embodiment, ICN up-regulates RTA promoter (RTAp) in a dose-dependent manner, such as in one embodiment, an increase in ICN from 0 to 200 μg, resulting in a 50 fold increase in concentration of RTAp, owing in another embodiment to the four identical RBP-Jκ binding sites within the RTA promoter. In one embodiment, truncated RTA promoter constructs lacking of RBP-Jκ-binding site are not responsive to ICN. Overexpression of ICN in KSHV latently infected PEL cells can interrupt in one embodiment, the viral latency and drive lytic replication to completion. In one embodiment induced expression of a truncated form of Notch1 fails to trigger full lytic reactivation of KSHV. In another embodiment, the latent state of the virus can be overcome in transfected cells. Interestingly, induction of the truncated Notch1 up-regulates a number of lytic genes. In one embodiment the demonstrated aberrant elevated levels of ICN in KSHV-positive B cells, where, in another embodiment ICN has an impact on either viral or cellular host factors. In one embodiment, LANA down-regulates ICN-mediated transactivation of the RTA promoter and shuts down ICN-mediated lytic replication. In one embodiment, ectopic expression of ICN triggers lytic replication and viral progeny production. In another embodiment, abnormal Notch1 signaling is linked to tumorigenesis through identification of a recurrent t (7;9)(q34;q34.3) chromosomal translocation involving human Notch1 gene that is found in certain human pre-T-cell acute lymphoblastic leukemias (T-ALL). In another embodiment, aberrant Notch signaling is involved in a wide variety of human neoplasms. In another embodiment ICN is highly expressed in KSHV-infected B cell.

In one embodiment, LANA, which is predominantly expressed in KSHV-infected B cells, stabilizes ICN, which explains the ICN accumulation in latently KSHV-infected cells. In another embodiment, elevated ICN functionally affects the proliferation of KSHV-positive B cells and in one embodiment, is critical for the survival of KSHV-infected primary B cells. In one embodiment, treatment with a γ-secretase inhibitor causes cell death in KSHV-infected primary B cells. In another embodiment, the γ-secretase inhibitor affects apoptosis of KSHV-infected endothelial KS cells. In one embodiment, the link between ICN levels and accelerated proliferation of B cells demonstrates a role for ICN in KSHV mediated B-cell proliferation. In another embodiment, increased levels of expression of cyclin D1 are a direct functional consequence of ICN levels, as cyclin D1 levels are dramatically suppressed when the production of ICN is inhibited in infected cells, using the methods and compositions described herein, as cyclin D1 is a major regulator of the G1/S transition.

In one embodiment, provided herein is a method for treating a virus-induced lymphoproliferative disease in a subject, comprising the step of administering to said subject a therapeutically effective amount of γ-secretase inhibitor, wherein said γ-secretase inhibitor prevents accumulation of intracellular Notch1 (ICN), and arrests infected host cells in the G1 phase thereby inhibits the proliferation of lymphoma.

In another embodiment, provided herein is a method for treating γ herpesvirus-related B lymphoma in a subject, comprising the step of administering to said subject a therapeutically effective amount of γ-secretase inhibitor, wherein said γ-secretase inhibitor prevents accumulation of intracellular Notch1 (ICN), and arrests infected cells in the G1 phase thereby inhibits the proliferation of lymphoma.

In one embodiment, the γ herpesvirus-related B lymphoma for which treatment is sought using the methods and compositions described herein, is primary effusion lymphoma (PEL), multicentric Castleman's disease (MCD), Epstein-Barr virus (EBV) transformed lymphoma or a combination thereof.

Primary effusion lymphoma (PEL) refers in one embodiment, to a large cell lymphoma, usually seen in human immunodeficiency virus (HIV)-infected patients. In one embodiment, PEL is characterized by various clinical, histomorphologic, and immunophenotypical features, and is associated with the human herpes virus. In another embodiment, PEL present as either a body cavity-based lymphomatous effusion or a solid tumor mass. In one embodiment "solid PEL" refers to an extranodal location; exceptionally rarely, they occur in lymph nodes. The majority of PEL consist of malignant cells of B-cell genotype; seldom of T-cell origin. Castleman's disease, also referred to in one embodiment, as angiofollicular or giant lymph node hyperplasia, is a clinically heterogeneous entity that can be either localized (unicentric), or multicentric. The multicentric form of the disease is an atypical lymphoproliferative disorder of a plasma cell type, and in one embodiment, is related to immune dysfunction. In another embodiment, mixture of both hyaline-vascular and plasma-cell variants can be found. In one embodiment, patients with MCD develop malignancies like Kaposi's sarcoma and non-Hodgkin's lymphoma. In one embodiment, MCD is histologically distinct from HHV8-negative MCD. In one embodiment, EBV infects B lymphocytes and establishes a latent infection. The viral genome enters the nucleus and persists in an episomal form. Six viral genes, termed EBNA 1-6 are expressed during this stage transforming in one embodiment the B cell into an immortal, continuously dividing cell. A small number of these "EBV-transformed" B cells circulate in another embodiment in the blood of healthy carriers in numbers that are regulated by the host's immune response. In another embodiment, immunosuppressed patients develop a polyclonal proliferation of EBV-transformed B cells.

In one embodiment, the virus which infection is sought to be treated using the methods and compositions described herein, is γ-herpesvirus, or Epstein-Barr virus (EBV), human herpesvirus 8 (HHV8), or their combination in other embodiments.

Figure 14:
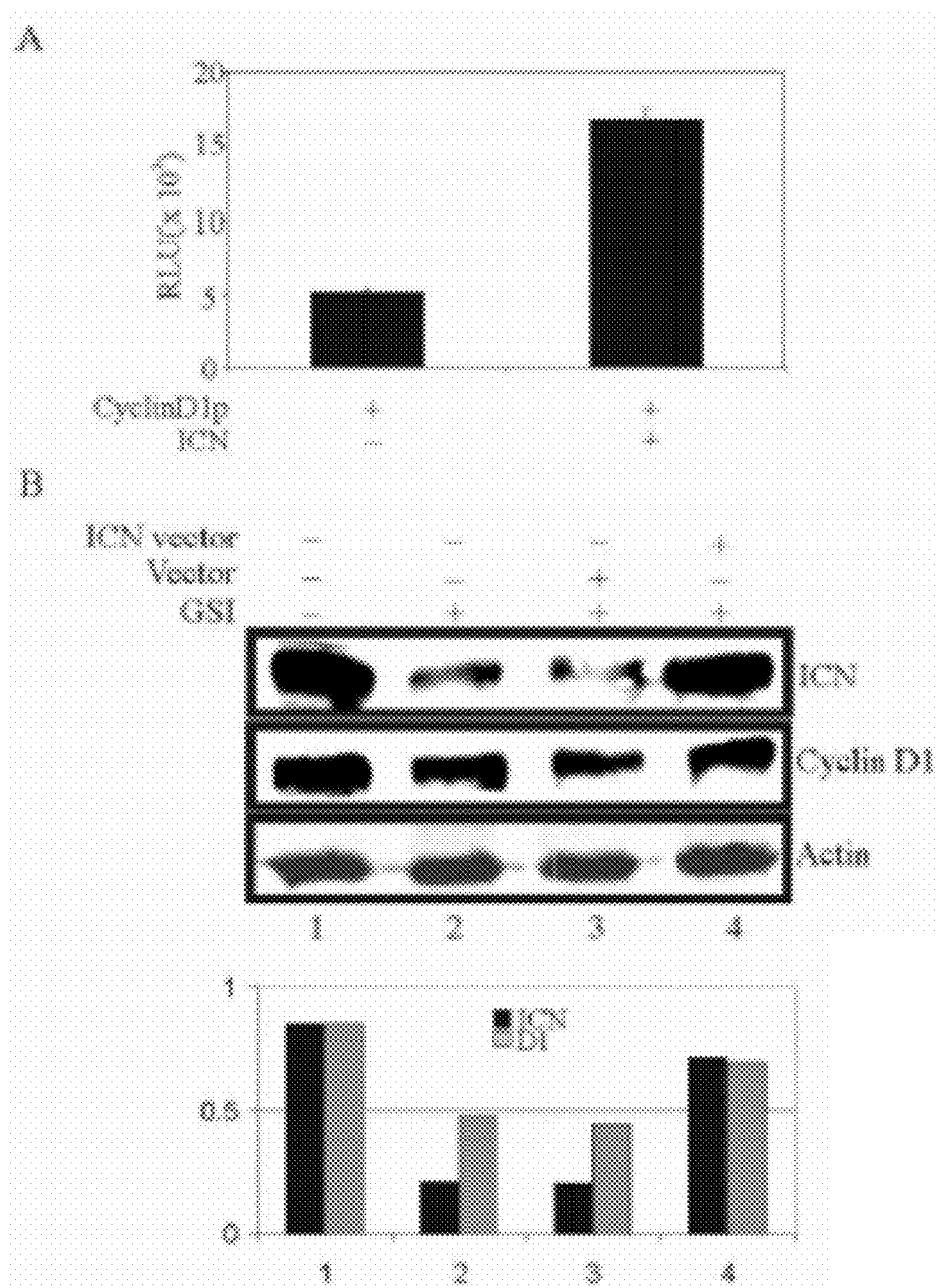
FIG. 14 shows (A) ICN up-regulates cyclin D1 promoter. One million U2OS cells were transfected with 0.5 μg cyclin D1 promoter reporter plasmid and 50 ng ICN expression vector or with 50 ng empty vector by the use of Lipofectamine 2000. At 24 h post transfection, cells were harvested and lysed for a reporter assay. RLU, relative light units. (B) Forced expression of ICN partially recovers the expression level of cyclin D1 in γ-secretase inhibitor (GSI)-treated BCBL1 cells. Lane 1, untreated BCBL1 cells; lane 2, BCBL1 cells with γ-secretase inhibitor; lane 3, BCBL1 cells with γ-secretase inhibitor transfected with empty vector; lane 4, BCBL1 cells with γ-secretase inhibitor transfected with pCDNA-ICN vector. The concentration of γ-secretase inhibitor was 20 μM, and the vector amount was 15 μg. The relative densities of ICN and cyclin D1 in each sample are also shown.
Figure 15:
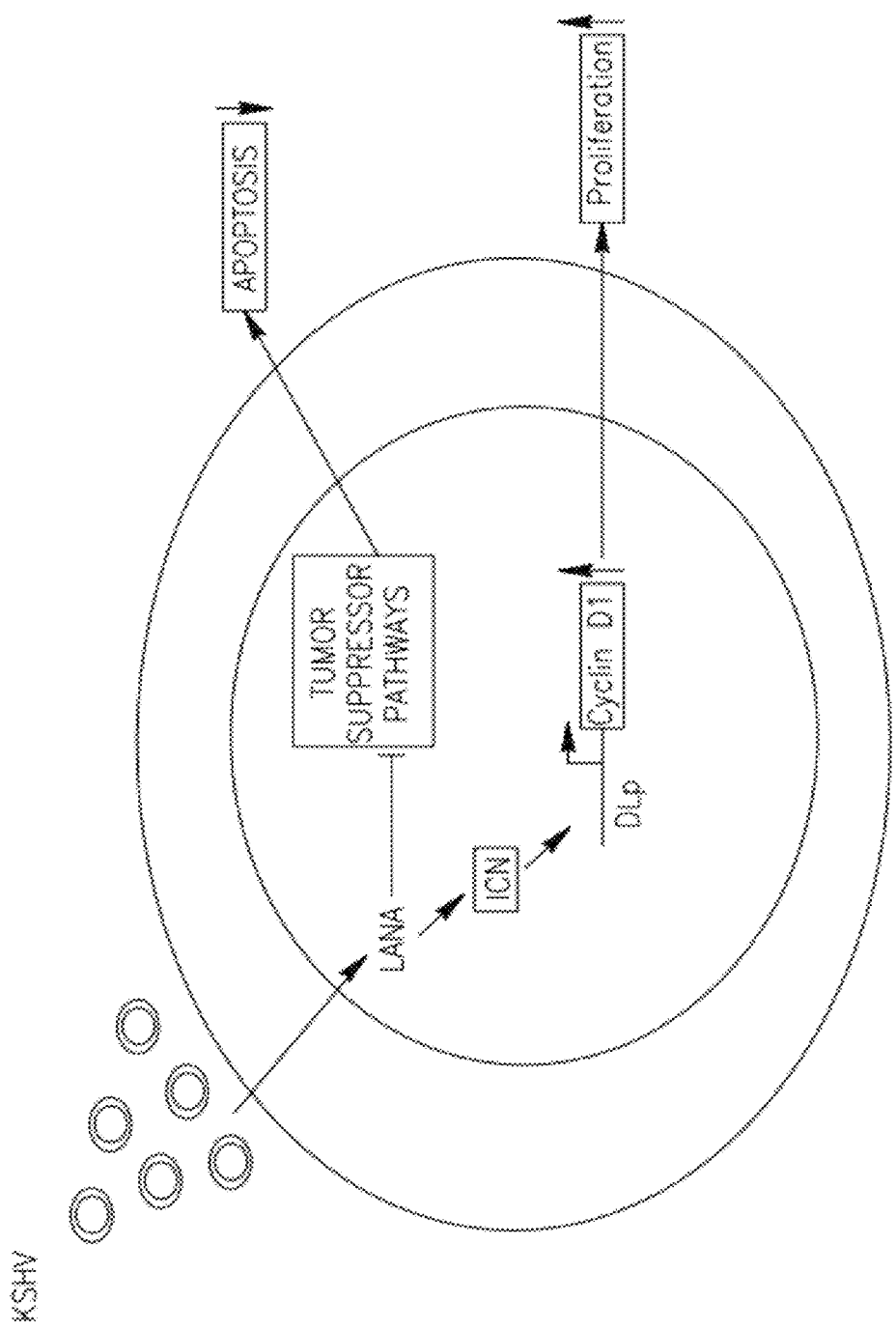
FIG. 15 shows a hypothetical model depicting how KSHV selectively usurps the function of the Notch signaling pathway, mediating oncogenesis. In this model, LANA mediates the accumulation of Notch ICN in KSHV-positive cells through enhancement of ICN stability, either directly or indirectly. This increased level of ICN up-regulates cyclin D1, resulting in proliferation of the infected cells.

In one embodiment, KSHV usurps Notch signaling to modulate viral gene expression through targeting of RBP-Jκ. In another embodiment KSHV directly induces ICN accumulation and usurps this signaling pathway to maintain the oncogenic phenotype of infected B-lymphoma cells. In one embodiment, ICN accumulates in latently KSHV-infected cells through a stabilization which is mediated by LANA. This increase in ICN levels is crucial for oncogenesis induced by KSHV, as seen by the significant increase in proliferation of KSHV-infected cells. The increase in proliferation mediated by ICN is due in another embodiment, to the up-regulation of cyclin D1 by ICN. This description provides an embodiment of virus-host interaction in which KSHV selectively usurps the function of a conserved cellular signaling pathway, achieving oncogenesis and providing a central role for Notch in KSHV-mediated lymphomagenesis (FIG. 14). In another embodiment, γ-secretase inhibitor dramatically reduces the proliferation of KSHV-positive cells and thus has therapeutic value in the treatment of KSHV-associated human cancers.

In one embodiment, the γ-secretase inhibitor used in the methods and compositions described herein, is N—[N-(3,5-difluorophenacetyl)-L-alanyl]-(S)-phenylglycine t-butyl ester (DAPT), or L-852,505, L-685,458, 2-[(1R)-1-[[(4-chlorophenyl)sulfony](2,5-difluorophenyl)amino]ethyl]-5-fluoro-benzenepropanoic acid (BMS-299897), or a combination thereof in other embodiments.

In another embodiment, the virus-induced lymphoproliferative disease sought to be treated using the compositions and methods described herein, is γ-herpesvirus-related B lymphoma.

In one embodiment, provided herein is a method for treating a virus-induced lymphoproliferative disease in a subject, comprising the step of administering to said subject a therapeutically effective amount of γ-secretase inhibitor, wherein said γ-secretase inhibitor prevents accumulation of intracellular Notch1 (ICN), and arrests infected host cells in the G1 phase thereby inhibits the proliferation of lymphoma; and further comprises the step of administering to the subject an agent capable reducing expression or function of latency associated nuclear antigen (LANA), cyclin D1 or their combination.

In one embodiment, the agent capable reducing expression or function of latency associated nuclear antigen (LANA), cyclin D1 or their combination in the context of describing compounds according to the invention refers to a compound that directly or indirectly inhibits, or in another embodiment suppresses the activity, function, ligand mediated transcriptional activation, or in another embodiment, signal transduction through the latency associated nuclear antigen (LANA), cyclin D1 or their combination. In one embodiment, the agent includes partial antagonists and in another embodiment full antagonists. In one embodiment, the term "full antagonist" refers to a compound that evokes the maximal inhibitory response from the latency associated nuclear antigen (LANA), cyclin D1 or their combination, even when there are spare (unbound) latency associated nuclear antigen (LANA), cyclin D1 or their combination present. In another embodiment, the term "partial antagonist" refers to a compound does not evoke the maximal inhibitory response from the latency associated nuclear antigen (LANA), cyclin D1 or their combination, even when present at concentrations sufficient to interact with the latency associated nuclear antigen (LANA), cyclin D1 or their combination present.

In one embodiment, reducing the expression or function of latency associated nuclear antigen (LANA), cyclin D1 or their combination, in the methods described herein comprises lowering the level of a protein or nucleic acid regulating the expression or function of said latency associated nuclear antigen (LANA), cyclin D1 or their combination. As used herein, "reduction" or "reduce" with respect to expression from a nucleic acid refers to a decrease in expression, or to decrease expression, in an amount that can be detected by assessing changes in RNA level, protein level, and phenotype. In one embodiment, reduction refers to a 5%, 10%, 25%, 50%, 75%, or more than 75% decrease in expression. A reduction in expression includes in another embodiment, complete inhibition of expression, whereby greater than 95% reduction of expression from a nucleic acid is achieved In another embodiment, the term "expression," with respect to expression of a gene or expression from a nucleic acid, which encodes for latency associated nuclear antigen (LANA), cyclin D1 or their combination, in the methods described herein, refers to production of a functional RNA molecule from a DNA molecule as well as production of a functional latency associated nuclear antigen (LANA), cyclin D1 or their combination, in the methods described herein from an mRNA molecule. Expression from a selected nucleic acid can be examined using standard methods known in the art. In an embodiment, RNA levels can be determined by Northern blot hybridization and in situ hybridization using the appropriate nucleic acid hybridization probes, while latency associated nuclear antigen (LANA), cyclin D1 levels or their combination, can be determine by antibody staining and western hybridization. Development of predetermined cellular structures that are affected by reduction in expression of selected nucleic acids can be assessed using various methods. In another embodiment, the expression of tissue-specific genes can be used to assess development of organs, differentiated tissues, and particular cellular structures. For example, expression of a thymus specific marker such as Rag-1 can be used to assess thymus development; and expression of pancreas-specific markers such as Fspondin and islet-1 can be used to assess pancreas development. (For standard methodologies, see H. W. Detrich III, M. Westerfield, and L. I. Zon, Methods in Cell Biology Vol. 59: The Zebrafish Biology, Academic Press. San Diego) Expression from a nucleic acid can be reduced by interfering with (1) any process necessary for RNA transcription, (2) RNA processing, (3) RNA transport across the nuclear membrane, (4) any process necessary for RNA translation, or (5) RNA degradation.

In one embodiment, the agent capable of reducing expression or function of latency associated nuclear antigen (LANA), cyclin D1 or their combination is a siRNA, a virus, polyamides, triple-helix-forming agents, antisense RNA, synthetic peptide nucleic acids (PNAs), agRNA, LNA/DNA copolymers, or a combination thereof.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the gene encoding the latency associated nuclear antigen (LANA), cyclin D1 described herein or their combination. In one embodiment, the agent used for reducing the level or function of latency associated nuclear antigen (LANA), cyclin D1 gene or their combination or its encoded protein, is a siRNA specific for the nucleic acid encoding latency associated nuclear antigen (LANA), cyclin D1 or their combination.

In one embodiment, the siRNA of the gene encoding the latency associated nuclear antigen (LANA), cyclin D1 or their combination, exhibit substantial complimentarity to its target sequence. In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the gene encoding latency associated nuclear antigen (LANA), cyclin D1 or their combination is sufficiently complimentary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, minor groove-binding N-methyl pyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes, are silenced in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the gene encoding the latency associated nuclear antigen (LANA), cyclin D1 or their combination in the methods and compositions described herein, is Py-Im polyamide specific for the coding region of the gene encoding latency associated nuclear antigen (LANA), cyclin D1 or their combination, or to regulatory sequences is unique to the gene encoding latency associated nuclear antigen (LANA), cyclin D1 or their combination in another embodiment. In another embodiment, the agent used to silence the gene encoding latency associated nuclear antigen (LANA), cyclin D1 or their combination in the methods and compositions described herein, is a synthetic polyamide nucleic acid (PNA) specific for the coding region of the gene encoding latency associated nuclear antigen (LANA), cyclin D1 or their combination, or to regulatory sequences is unique to the gene encoding latency associated nuclear antigen (LANA), cyclin D1 or their combination in another embodiment.

In one embodiment, the polyamides used in the compositions and methods described herein, which, in another embodiment are referred to as "peptide nucleic acid" (PNA) or "synthetic peptide nucleic acids", is an alkylating Py-Im polyamides that show sequence-specific DNA alkylation. In another embodiment, alkylation of a template strand in the coding region of the gene encoding latency associated nuclear antigen (LANA), cyclin D1 or their combination, by Py-Im polyamide-cyclopropylpyrroloindole (CPI) conjugates with a vinyl linker results in the production of truncated mRNA, effectively inhibiting transcription of the gene encoding latency associated nuclear antigen (LANA), cyclin D1 or their combination in vitro. In one embodiment, Py-Im tetrahydro-cyclopropabenzindolone (CBI) conjugates with indole linkers are the alkylating polyamides used as the agent capable of inhibiting the expression or function of the gene encoding latency associated nuclear antigen (LANA), cyclin D1 or their combination, because indole-CBI has increased chemical stability under acidic and basic conditions.

Oligodeoxynucleotides have been described which inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are generally called triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of the gene encoding latency associated nuclear antigen (LANA), cyclin D1 or their combination.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the agent capable of inhibiting the expression or function of the gene encoding latency associated nuclear antigen (LANA), cyclin D1 or their combination is a triple-helix-forming agents. In another embodiment, the triple-helix-forming agents are oligonucleotides. In one embodiment, oligonucleotide-mediated triplex formation prevent transcription factor binding to promoter sites and block mRNA synthesis in vitro and in vivo. In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment oligomeric antisense compounds, particularly oligonucleotides, are used in modulating the function of nucleic acid molecules encoding latency associated nuclear antigen (LANA), cyclin D1 or their combination, ultimately modulating the produced amount of latency associated nuclear antigen (LANA), cyclin D1 or their combination. This is accomplished by providing antisense compounds which specifically hybridize with one or more nucleic acids encoding latency associated nuclear antigen (LANA), cyclin D1 or their combination. As used herein, the terms "target nucleic acid" and "nucleic acid encoding latency associated nuclear antigen (LANA), cyclin D1 or their combination" encompass DNA encoding latency associated nuclear antigen (LANA), cyclin D1 or their combination, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of latency associated nuclear antigen (LANA), cyclin D1 or their combination. In one embodiment, inhibition of gene expression is preferred and mRNA is a preferred target. In one embodiment, since many genes (including the gene encoding latency associated nuclear antigen (LANA), cyclin D1 or their combination) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding latency associated nuclear antigen (LANA), cyclin D1 or their combination. The targeting process also includes in another embodiment, determination of a site or sites within this gene for the antisense interaction to occur such that the desired effect, e.g., inhibition of expression of the protein such as the latency associated nuclear antigen (LANA), cyclin D1 or their combination, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding the latency associated nuclear antigen (LANA), cyclin D1 or their combination, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as lymphoproliferative disease, MCD or PEL syndrome. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene expression, such as the gene encoding latency associated nuclear antigen (LANA), cyclin D1 or their combination, with extreme specificity, are used by those of ordinary skill to elucidate the function of particular genes. Antisense compounds are used in another embodiment, to distinguish between functions of various members of a biological pathway. Antisense modulation has, in one embodiment of the agents described in the methods and compositions described herein, been harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans. In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the oligonucleotides used in the methods and compositions described herein, are synthetic peptide nucleic acids (PNAs) which interact with the nucleotide sequence of the gene encoding latency associated nuclear antigen (LANA), cyclin D1 or their combination, in a sequence-specific manner and silence expression or function of the gene encoding latency associated nuclear antigen (LANA), cyclin D1 or their combination. In another embodiment, the oligonucleotides used in the methods and compositions described herein, are locked nucleic acid (LNA), which interact with the nucleotide sequence the gene encoding latency associated nuclear antigen (LANA), cyclin D1 or their combination, forming a LNA/DNA co-polymer, in a sequence-specific manner and substantially silence expression or function of latency associated nuclear antigen (LANA), cyclin D1 or their combination.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein.

In one embodiment, the target specific regions of the agent that is able to inhibit gene expression, such as the gene encoding latency associated nuclear antigen (LANA), cyclin D1 or their combination, may comprise LNA and/or PNA and the arm region comprise DNA, with the agent further comprising a destabilizing moiety.

In another embodiment, the agent capable of inhibiting expression or function of the gene encoding latency associated nuclear antigen (LANA), cyclin D1 or their combination, or latency associated nuclear antigen (LANA), cyclin D1 or their combination, is an agPNA. In another embodiment, this antibody is referred to as antigenic PNA.

In one embodiment, the term "treatment" refers to any manner in which one or more of the symptoms of a disease or disorder are ameliorated or otherwise beneficially altered. Treatment also encompasses any pharmaceutical use of the compositions and methods described herein, such as use for treating hyperproliferating tissue or neovascularization mediated diseases or disorders, or diseases or disorders in which hyperproliferating tissue or neovascularization is related.

In another embodiment, treating comprises inhibiting or suppressing production of intracellular Notch1 (ICN) resulting from viral infection, comprising contacting the infected host cell with an effective amount of a γ-secretase inhibitor, wherein said γ-secretase inhibitor arrests growth of infected host at the G1 phase.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. Therefore, in one embodiment, the invention provides a treating a virus-induced lymphoproliferative disease in a subject, comprising the step of administering to said subject a therapeutically effective amount of γ-secretase inhibitor, wherein said γ-secretase inhibitor prevents accumulation of intracellular Notch1 (ICN), and arrests infected host cells in the G1 phase thereby inhibits the proliferation of lymphoma. In another embodiment, the virus inducing the lymphoproliferative disease in a subject, is γ-herpesvirus, Epstein-Barr virus (EBV), human herpesvirus 8 (HHV8), or their combination.

In one embodiment, the term "contacting a cell", refers to any exposure of a host cell to a peptide, nucleic acid, or composition of this invention. Cells may be in direct contact with compounds and compositions of the invention, or exposed indirectly, through methods well described in the art. For example, infected host cells grown in media in vitro, wherein the media is supplemented with any of agents or compositions described herein would be an example of a method of contacting a cell, considered a part of this invention. Another example would be oral or parenteral administration of a peptide, nucleic acid, compound or composition, whose administration results in vivo cellular exposure to these compounds, within specific sites within a body. Such administration is also considered as part of this invention, as part of what is meant by the phrase "contacting an infected host cell".

In one embodiment, the term "viral infection" or "infection", refers to the introduction of a virus into cells or tissues, e.g., γ-herpesvirus. In another embodiment, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. In one embodiment, a virus may infect an organ such as the thyroid or certain cells, such as lymphocytes in another embodiment. In one embodiment, the term "infection" refers to the virus capability of transfecting a host cell In one embodiment, "transfection" refers to a cell that has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary or other cell that is capable of stable growth in vitro for many generations. An organism, such as a plant or animal, that has been transformed with exogenous DNA is termed "transgenic".

Figure 12:
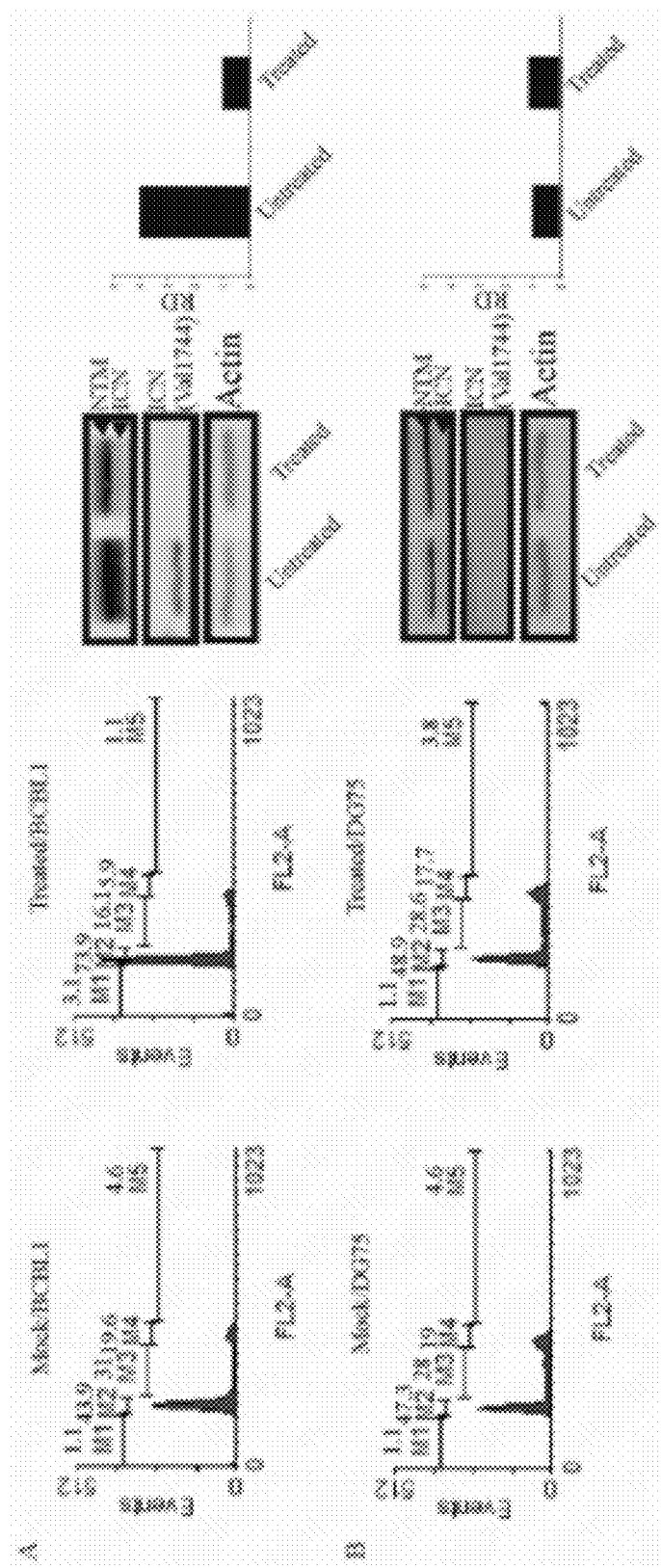
FIG. 12 shows FACS analysis showing cell cycle distributions of mock-treated and 7-secretase inhibitor-treated BCBL1 cells (A) and DG75 cells (B). At 48 h post treatment, cells were harvested, fixed, and stained with propidium iodide. M2, M3, and M4 represent the G1, S, and G2/M populations of cells, respectively. M1 and M5 represent hypo- and hypernucleated cells, respectively. The percentage of cells in each different phase is indicated. Western blot analysis indicates the ICN levels in γ-secretase inhibitor-treated DG75 cells or BCBL1 cells. The relative density (RD) of ICN in each sample is also shown.

In one embodiment, γ-secretase inhibitor slows down proliferation of the KSHV-positive B lymphocytes dramatically. In another embodiment, γ-secretase inhibitor-treated B lymphocytes are arrested at G1 phase of the cell cycle (FIG. 12A). In another embodiment, ICN levels are decreased in infected host cells treated with γ-secretase inhibitor (FIG. 12A). In contrast, the uninfected cells have similar cell cycle patterns for mock-treated cells and those treated with γ-secretase inhibitor. In another embodiment, the uncleaved transmembrane form of Notch1 is the predominant signal in the infected cells (FIG. 12B). In one embodiment, there is no active cleavage of Notch1 to the activated intracellular form in indicating the reason γ-secretase inhibitor was ineffective in regulation of cell proliferation of KSHV-negative cells.

In one embodiment, the agents described hereinabove are used in the compositions described herein. In another embodiment, provided herein is a composition for the treatment of a malignancy associated with a viral transfection, comprising: a therapeutically effective amount of a γ-secretase inhibitor, a pharmaceutically acceptable carrier, excipient, flow agent, processing aid, diluent or a combination thereof. In one embodiment, the malignancy associated with said viral transfection is Kaposi's sarcoma (KS), primary effusion lymphoma (PEL), multicentric Castleman's disease (MCD), Epstein-Barr virus (EBV) transformed lymphoma or a combination thereof. In another embodiment, the transfecting virus is γ-herpesvirus, Epstein-Barr virus (EBV), human herpesvirus 8 (HHV8), or their combination. In one embodiment, the compositions described herein, which are used in the methods described herein, further comprise an agent capable reducing expression or function of latency associated nuclear antigen (LANA), cyclin D1 or their combination, wherein the agent is a siRNA, a virus, polyamides, triple-helix-forming agents, antisense RNA, synthetic peptide nucleic acids (PNAs), agRNA, LNA/DNA copolymers, or a combination thereof.

In one embodiment, the compositions described herein, used in the invention further comprise a carrier, or excipient, lubricant, flow aid, processing aid or diluent in other embodiments, wherein the carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetener, a film forming agent, or any combination thereof.

In one embodiment, the composition is a particulate composition coated with a polymer (e.g., poloxamers or poloxamines). Other embodiments of the compositions of the invention incorporate particulate forms protective coatings, protease inhibitors or permeation enhancers for various routes of administration, including parenteral, pulmonary, nasal opthalmic and oral. In one embodiment the pharmaceutical composition is administered parenterally, paracancerally, transmucosally, transdermally, intramuscularly, intravenously, intradermally, subcutaneously, intraperitonealy, intraventricularly, or intracranially.

In one embodiment, the compositions of this invention may be in the form of a pellet, a tablet, a capsule, a solution, a suspension, a dispersion, an emulsion, an elixir, a gel, an ointment, a cream, or a suppository.

In another embodiment, the composition is in a form suitable for oral, intravenous, intraaorterial, intramuscular, subcutaneous, parenteral, transmucosal, transdermal, or topical administration. In one embodiment the composition is a controlled release composition. In another embodiment, the composition is an immediate release composition. In one embodiment, the composition is a liquid dosage form. In another embodiment, the composition is a solid dosage form.

In one embodiment, the term "pharmaceutically acceptable carriers" includes, but is not limited to, may refer to 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

In one embodiment, the compounds of this invention may include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The pharmaceutical preparations of the invention can be prepared by known dissolving, mixing, granulating, or tablet-forming processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic is bases as isopropylamine, trimethylamine, 2-ethylamino ethanol, histidine, procaine, and the like.

The active agent is administered in another embodiment, in a therapeutically effective amount. The actual amount administered, and the rate and time-course of administration, will depend in one embodiment, on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used in another embodiment, to deliver the active agent more specifically to certain types of cell, by the use of targeting systems such as antibodies or cell specific ligands. Targeting may be desirable in one embodiment, for a variety of reasons, e.g. if the agent is unacceptably toxic, or if it would otherwise require too high a dosage, or if it would not otherwise be able to enter the target cells.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound sucrose as a sweetening agent methyl and propylparabens as preservatives, a dye and flavoring, such as cherry or orange flavor. In addition, the active compounds may be incorporated into sustained-release, pulsed release, controlled release or postponed release preparations and formulations.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, the composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Such compositions are in one embodiment liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors, or permeation enhancers for various routes of administration, including parenteral, pulmonary, nasal, and oral.

In another embodiment, the compositions of this invention comprise one or more, pharmaceutically acceptable carrier materials. In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods:
Antibodies, Cell Lines, Plasmids and Tissue

KSHV Rta rabbit polyclonal antibody was provided by Gary S. Hayward (Johns Hopkins University School of Medicine). KSHV Rta mouse monoclonal antibody was a kind gift from Koichi Yamanishi (Osaka University, Osaka, Japan). Human polyclonal serum which recognizes LANA is designated as HS and was provided by Gary Nabel (Vaccine Institute, NIH, Bethesda, Md.). Notch rabbit anti-serum was provided by Jon C. Aster and Elliot Kieff (Brigham and Women's Hospital, Boston, Mass.). Val1744 antibody was purchased from Cell Signaling Technology Inc, Beverly, Mass.

Human embryonic kidney fibroblast 293 cell was obtained from Jon Aster (Brigham and Women's Hospital, Boston, Mass.). BJAB is KSHV-negative B cell lines isolated from Burkitt's lymphoma and was provided by Elliott Kieff (Harvard Medical School, Boston, Mass.). BCBL1 and BC3 are KSHV-positive body cavity-based lymphoma-derived cell lines obtained from Dr. Don Ganem and the American Type Culture Collection, respectively. JSC1 is a kind gift from Richard F. Ambinder (Johns Hopkins University School of Medicine, Baltimore, Md.). Vero cells stably infected with Bac36 (Vero/Bac36) were provided by Shou-jiang Gao (The University of Texas Health Science Center, San Antonio, Tex.). A human osteosarcoma cell line U2OS was obtained from the American Type Culture Collection.

Human embryonic kidney fibroblast 293 and 293T cells were grown in high-glucose DMEM supplemented with 5% bovine growth serum (BGS, Hyclone Inc. Logan, Utah), 2 mM L-glutamine, 25 U/ml penicillin, and 25 µg/ml streptomycin. Ramos, Loukes, DG75, BCBL1, BC3, and JSC1 were grown in RPMI 1640 medium supplemented with 10% BGS, 2 mM L-glutamine, 25 U/ml penicillin, and 25 µg/ml streptomycin.

A γ-secretase inhibitor (N—[N-(3,5-difluorophenacetyl-L-alanyl)]-S-phenylglycine t-butyl ester, (DAPT)) was purchased from Calbiochem Inc. (San Diego, Calif.).

HA-tagged Notch ICN pflu-ICN and untagged pCDNA3.1-ICN expression vector, full-length Notch1, Delta E, and Delta EA constructs were described previously (Aster et al., 1997). Specifically, ICN is encoded by a cDNA consisting of the first two codons of NOTCH1 fused to codon 1770, which lies 24 amino acids internal to the transmembrane domain (Aster et al., 1997). Reporter plasmid of RTA promoter was provided by Ren Sun (University of California at Los Angeles) (Deng et al., 2000). Myc-tagged LANA pA3M-LANA and truncation versions of RTA promoters were described previously (Lan et al., 2005a, 2005b; Lan et al., 2004).

Kaposi's sarcoma tissues were obtained from archived samples at the Hospital of University of Pennsylvania Department of Pathology and Laboratory Medicine and with diagnosis of KS by the resident pathologist. All tissue samples are AIDS-associated Kaposi's sarcoma.

Hemagglutinin-tagged Notch ICN, pflu-ICN, and untagged pCDNA3.1-ICN expression vector were described previously (3). Myc-tagged LANA (pA3MLANA) was described previously (31-33). The cyclin D1 reporter plasmid was a kind gift from Nancy Raab-Traub (University of North Carolina, Chapel Hill, N.C.).

Transfection

BCBL1 or Vero/Bac36 cells were transfected by electroporation using a Bio-Rad Gene Pulser II electroporator. Ten million cells harvested in exponential phase were collected and washed in phosphate-buffered saline and then resuspended in 400 µl of RPMI or DMEM with DNA for transfection. Resuspended cells were transferred to a 0.4-cm cuvette and electroporated at 975 µF and 220 V. The electroporated cells were then transferred to 10 ml of complete medium followed by incubation at 37° C. and 5% CO2. Transfections were harvested after 24 h and assayed for activity.

For certain Examples; DG75 or BCBL1 cells were transfected by electroporation, using a Bio-Rad Gene Pulser II electroporator. Ten million cells harvested in exponential phase were collected and washed in phosphate-buffered saline (PBS) and then resuspended in 400 µl of RPMI or Dulbecco's modified Eagle's medium with DNA for transfection. Resuspended cells were transferred to a 0.4-cm cuvette and electroporated at 975 µF and 220 or 250 V. The electroporated cells were then transferred to 10 ml of complete medium, followed by incubation at 37° C. and 5% CO2. Transfected cells were harvested after 24 h and assayed for activity Luciferase Assay U2OS cells were collected at 70% confluency. One million 509 cells were collected for transfection by using lipofectamine. The cells were subsequently lysed with 200-μl Reporter Lysis Buffer (Promega, Inc. Madison, Wis.). Forty microliters of the lysate was mixed with 100 μl of luciferase assay reagent. Luminescence was measured for 10 s by the Opticomp I luminometer (MGM Instruments, Inc. Hamden, Conn.). The lysates were also tested at varying dilutions to ensure that luciferase activity was within the linear range of the assay. The results shown represent experiments performed in triplicate.

Induction of KSHV Lytic Replication and Infection

To prepare KSHV virus particles, we collected approximately 500 million exponentially growing BCBL1 cells for induction.

Real-Time RT-PCR

Real-time qPCR was used to make a relative quantitative comparison of Notch levels in different cell lines or RTA levels in different transfected or TPA-induced BCBL1 cells. The procedure and method for calculation were described previously (Lan, K., D. A. Kuppers, S. C. Verma, N. Sharma, M. Murakami, and E. S. Robertson. 2005. *Induction of Kaposi's sarcoma-associated herpesvirus latency-associated nuclear antigen by the lytic transactivator RTA: a novel mechanism for establishment of latency*. J. Virol. 79:7453-7465.). The primers in this experiment were for Notch (5' GGCCFTCAAAGTGTCTGAGG 3' [SEQ ID NO. 1], 5' CGGAACTTCTTGGTCTCCAG 3' [SEQ NO.2]), Rta (5' TATCCAGGAAGCGGTCTCAT 3' [SEQ ID NO.4], 5' GGGTTAAAGGGGATGATGCT 3' [SEQ ID NO. 5]), and β-actin (5' GCTCGTCGTCGACAACGGCTC 3' [SEQ ID NO. 6], 5' CAAACATGATCTGGGTCATCTTCTC 3' [SEQ ID NO. 7]).

Immunofluorescence

Immunofluorescent assays were performed essentially as described previously (Lan, K., D. A. Kuppers, and E. S. Robertson. 2005. *Kaposi's sarcoma-associated herpesvirus reactivation is regulated by interaction of latency-associated nuclear antigen with recombination signal sequence-binding protein Jkappa, the major downstream effector of the Notch signaling pathway*. J. Virol. 79:3468-3478, Lan, K., D. A. Kuppers, S. C. Verma, N. Sharma, M. Murakami, and E. S. Robertson. 2005. *Induction of Kaposi's sarcoma-associated herpesvirus latency-associated nuclear antigen by the lytic transactivator RTA: a novel mechanism for establishment of latency*. J. Virol. 79:7453-7465; Lan, K., D. A. Kuppers, S. C. Verma, and E. S. Robertson. 2004. *Kaposi's sarcoma-associated herpesvirus-encoded latency-associated nuclear antigen inhibits lytic replication by targeting Rta: a potential mechanism for virus-mediated control of latency*. J. Virol. 78:6585-6594.). Slides were visualized with an Olympus XI70 inverted fluorescence microscope (Olympus Inc. Melville, N.Y.) and photographed using a digital PixelFly camera and software (Cooke Inc. Warren, Mich.).

Flow Cytometry

All flow cytometric analysis was conducted on FACS Calibur cytometer (Becton Dickinson, San Jose, Calif.) and analysis with FlowJo software (Tree Star, Ashland, Oreg.). For GFP quantification, cells were fixed with 3% paraformaldehyde. Rehyrdrade in PBS containing 1% BSA. Cells were washed thoroughly and analyzed on a flow cytometer equipped with 488-nm Argon laser light source and a 515-nm band pass filter for GFP fluorescence. Total 10,000 events were acquired for analysis using CellQuest software. Cells were properly gated as described earlier, and histogram plot of GFP fluorescence (x axis) versus counts (y axis) has been shown in logarithmic fluorescence intensity.

For the determination of the expression of RTA protein, 7 million cells were fixed in methanol and then permeabilized. Cells were incubated with polyclonal anti-RTA for 2 h at room temperature and then with FITC-conjugated isotype-specific secondary antibody for detecting the respective protein levels for 1 h. Cells were washed thoroughly and analyzed on a flow cytometer equipped with 488-nm Argon laser light source and a 515-nm band pass filter for FITC fluorescence. Total 10,000 events were acquired for analysis using CellQuest software. Cells were properly gated as described earlier, and histogram plot of FITC fluorescence (x axis) versus counts (y axis) has been shown in logarithmic fluorescence intensity Example 1

Expression Levels of Notch ICN are Elevated in KSHV-Positive B Cells

Notch is a transmembrane receptor whose signaling is triggered by ligand binding. Typically, protease-based cleavages lead to the production of ICN, which then translocates to the nucleus and binds to RBP-Jκ to modulate the expression of its downstream genes.

To determine if ICN is up-regulated in KSHV-infected PEL cell lines, Western blot analysis of three cell lines, BCBL1, BC3, and JSC1, which are all latently infected with KSHV was performed. The results showed dramatically elevated levels of ICN in KSHV-positive PEL cells when compared to the KSHV-negative B lymphoma cell line BJAB based on signals from either the ICN polyclonal anti-serum against intracellular Notch or the ICN-specific antibody Val1744 which detects the approximately 110 kDa Notch1 cleaved at V1744 by gamma-secretases (FIG. 1B). As expected, Notch-1 ICN up-regulation was also seen in paraffin-embedded tissue section stained from KS lesion in a Kaposi's sarcoma patient by immunohistochemistry (FIG. 1C, left panel). In this immunostaining, ICN expression correlated with KSHV infection as determined by the corresponding signals for LANA when compared with the reduced ICN signals in the adjacent normal tissue not infected with KSHV (FIG. 1C, compare left and right panels). From HE staining, characteristic cells with spindle shape are visualized in the tumor (FIG. 1C, top panels).

Example 2

Figure 2:
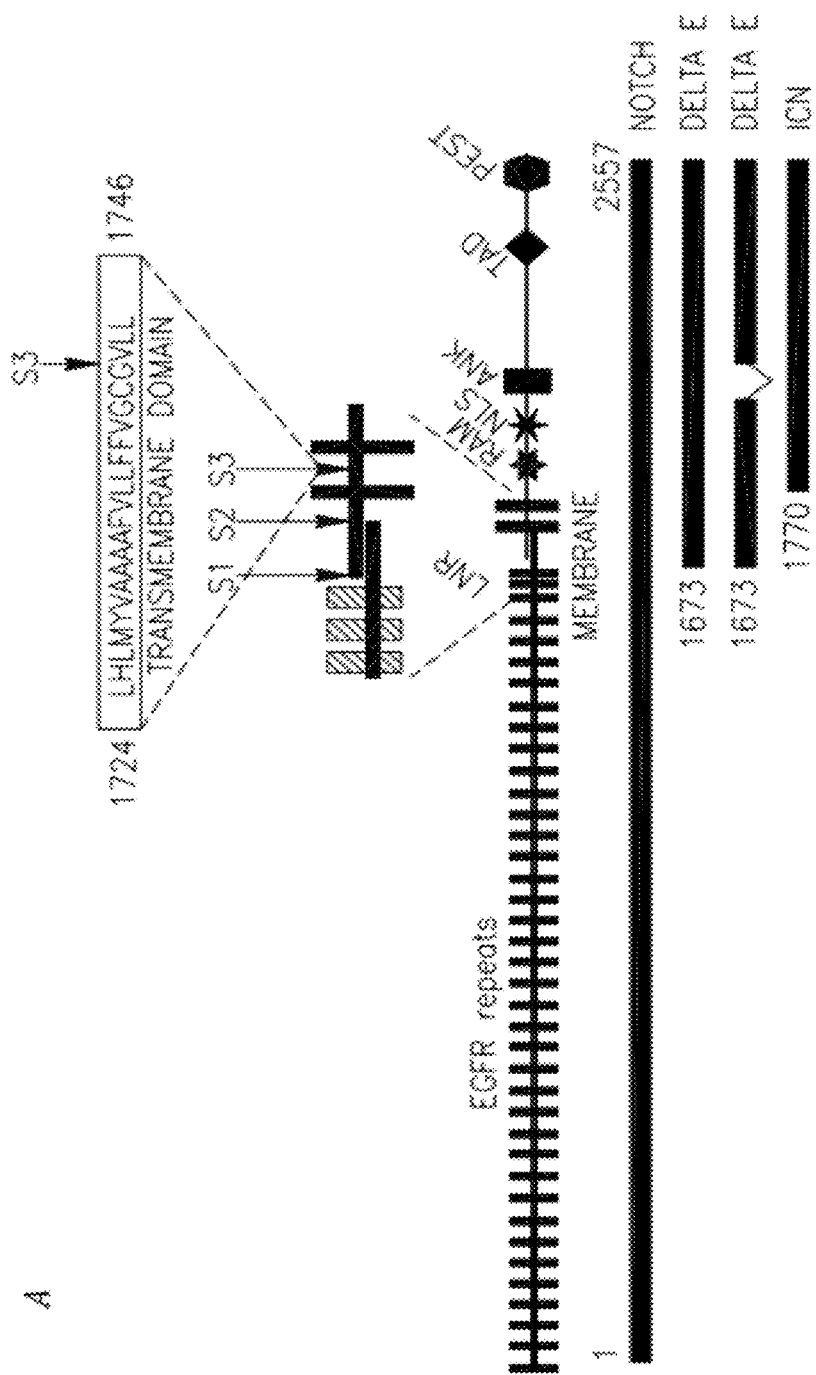
FIG. 2 shows ICN activates RTA promoter in a dose-dependent manner (A) Scheme to show the Notch expression constructs used for luciferase assay. Delta E is encoded by a cDNA consisting of codons 1-22 fused to codons 1673-2555 and is predicted to result in the synthesis of a mature polypeptide with an amino terminus lying 61amino acids external to the transmembrane domain. Delta EA has an additional deletion of ankyrin repeats. ICN is encoded by a cDNA consisting of the first two codons of NOTCH1 fused to codon 1770, which lies 24 amino acids internal to the transmembrane domain (Aster et al., 1997). In the diagram, proteolytic cleavage by furin at site S1 produces two subunits, ECN and NTM, which remain non-covalently associated at the cell surface. Sites S2 and S3 identify the sites of proteolytic cleavage mediated by metalloproteases and presenilins induced upon activation by ligand. Cleavage at S3 yields activated form of Notch ICN (Schroeter et al., 1998). (B) Luciferase assay: 1 million of U2OS cells were transfected with 0.5-µg RTA promoter reporter plasmid along with increasing amount of full-length Notch, Delta E, Delta EA or ICN expression vector (0 ng, 10 ng, 20 ng, 50 ng, 100 ng, 200 ng) by lipofectamine 2000. Twenty four hours post-transfection, cells were harvested and lysed for reporter assay.
Figure 2:
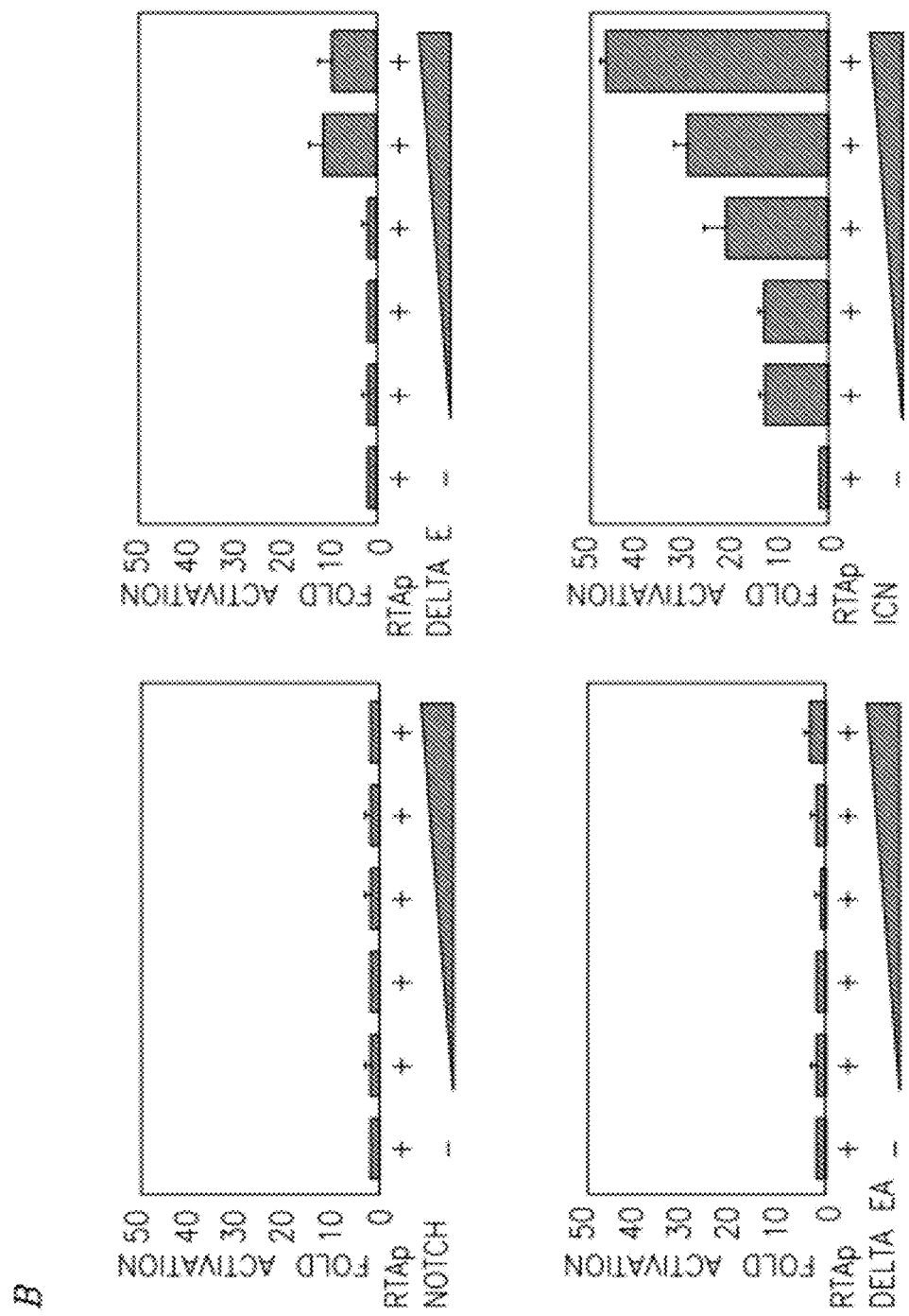

ICN Activates RTA Promoter in a Dose-Dependent Manner and Ectopic Expression of ICN Reactivates KSHV from Latency A determination was made to examine if Notch1 and specific truncations of Notch1 which includes ICN can reactivate KSHV (FIG. 2A). Interestingly, results from the reporter assays showed that ICN specifically up-regulated the RTA promoter in a dose-dependent manner (FIG. 2B). This suggested that increased ICN may potentially activate RTA expression in KSHV-infected cells leading to viral reactivation. However, full-length Notch as well as a truncated transmembrane form of Notch1 with ankyrin repeats deleted had little or no effect on the RTA promoter (FIG. 2B). Additionally, truncated Notch1 delta E construct can activate RTA promoter when delivered at high doses, but the activation is much less efficient when compared to the activation seen with ICN (FIG. 2B).

Figure 3:
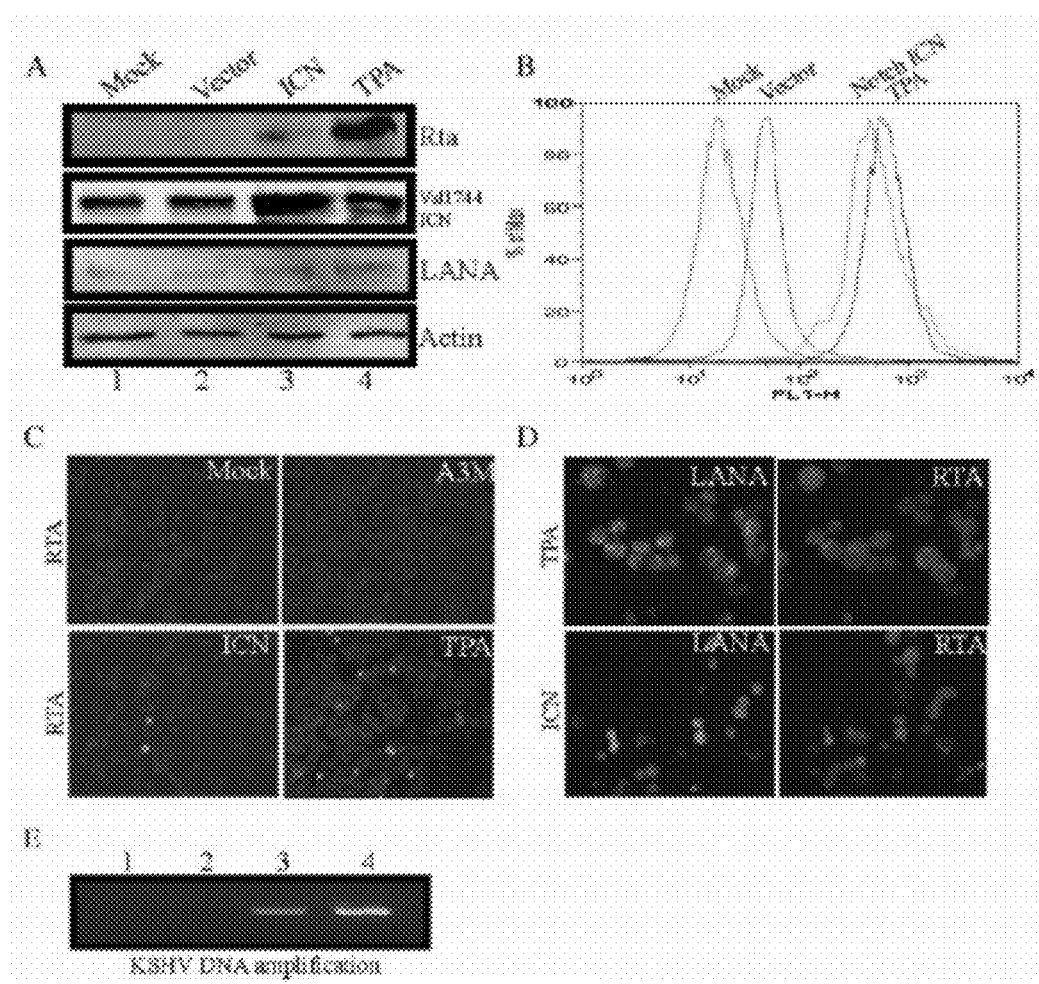
FIG. 3 shows Ectopic expression of ICN can activate KSHV. Fifteen million BCBL1 cells were transfected with mock, empty vector pA3M, and ICN, respectively or induced with TPA. Twenty four hours post-transfection and induction, cells were harvested and used for making lysates for Western blot analysis (A) and stained with rabbit anti-RTA serum and goat anti-rabbit FITC for FACS analysis (B) as well as immunofluorescence assay to detect RTA expression (C). (D) Supernatants from ICN transfected BCBL1 or TPA-induced BCBL1 cells were harvested and concentrated for infection of 293 cells. Twelve hours post-infection, cells were collected and fixed for immunofluorescence assay to detect LANA and RTA expression. (E) PCR showing the presence of KSHV viral DNA in the supernatants from ICN transfected (lane 3) and TPA-induced (lane 4) BCBL1 cells instead of mock (lane 1) and empty vector pA3M (lane 2)-transfected BCBL1 cells. The primers were 5' CCT TGG TGC GTT TAACAACA 3' (SEQ ID NO. 1) and 5' TTATGTAACGCGGAACTCCA 3' (SEQ ID NO. 2).

To test if ICN drive lytic replication, BCBL1 cells were transfected with an ICN expression vector or induced with TPA as a positive control. TPA is a chemical inducer which is capable of inducing RTA expression and complete viral lytic replication cycle. Twelve hours post-transfection and induction, cells were harvested for analysis. Western blot analysis showed that RTA was strongly expressed in TPA-induced cells as expected (FIG. 3A, lane 4). RTA was also detected in ICN-transfected cells (FIG. 3A, lane 3), however the level of RTA induction by ICN was lower than that seen for TPA-induced cells, likely as a result of the transfection efficiency of the BCBL1 cell line using the ICN expression construct. These results were further corroborated by FACS and immunostaining analyses. RTA signal was clearly detected in ICN-transfected BCBL1 cells. However, the number of cells expressing RTA was less than those found positive in TPA-induced BCBL1 cells (FIGS. 3B, C). As expected, there are no detectable levels of RTA found in mock or empty vector-transfected BCBL1 cells (FIGS. 3B, C).

To determine if RTA induction resulted in production of viral particles, the supernatants of the transfected or induced cells were collected and concentrated and used to infect fresh cells. Immunostaining analysis demonstrated that RTA and LANA were detected in infected cells incubated with supernatant from TPA-induced BCBL1 (FIG. 3D, upper panel) or with supernatant obtained from ICN-transfected BCBL1 (FIG. 3D, 185 bottom panel) 12-h post-infection. This indicated that KSHV infectious virions were produced and secreted in both supernatants and that increased expression of ICN can drive the full cycle of viral lytic replication. In addition, viral DNA was also detected in both supernatants (FIG. 3E, lanes 3 and 4, respectively), however, viral DNA was not detected in the supernatants from mock and empty vector-transfected BCBL1 cells (FIG. 3E, lanes 1 and 2).

Figure 4:
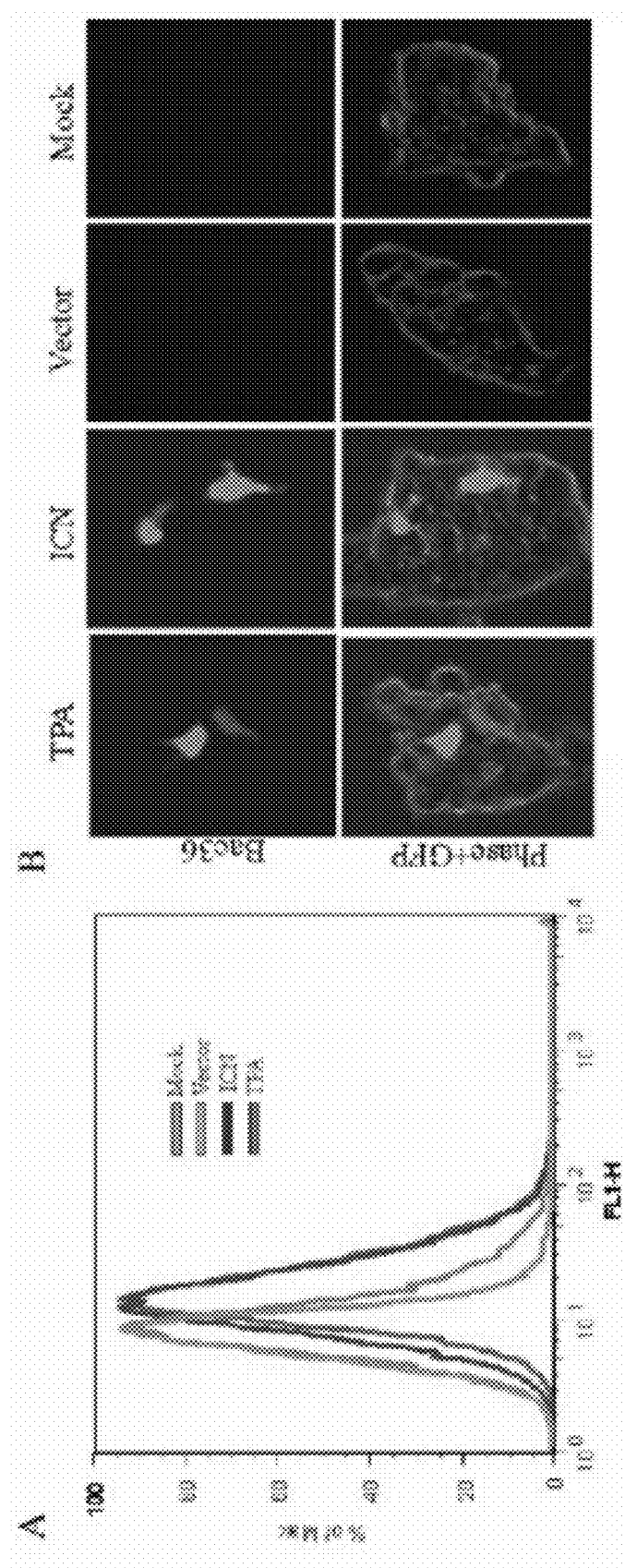
FIG. 4 shows FACS analysis showing the GFP expression in infected 293 cells with the supernatants from mock, pA3M, and ICN-transfected or TPA-induced Vero cells which were stably infected with Bac36. (B) Direct microscope to check GFP expression in the above infected cells.

To further support these studies, stably infected Vero cells were employed with the KSHV-GFP Bac36 recombinant virus to test the ability of ICN to regulate viral life cycle since there is a much higher transfection efficiency for Vero cells. Vero/Bac36 cells were transfected with ICN or empty vector, and TPA-induced Vero/Bac36 cells were also used as a positive control. Four days post-transfection or induction, the supernatants were collected and concentrated for infection of cells. GFP can be directly observed as a marker for viral infection. Clearly, GFP signals were detected by FACS analysis in the infected cells with supernatants from ICN-transfected Vero/Bac36 or TPA-induced Vero/Bac36 (FIG. 4A). However, no detectable levels of GFP signals were found in cells infected with supernatants from mock or empty vector-transfected Vero/Bac36 (FIG. 4A). In addition, 293 cells infected with Bac36 were also directly observed by GFP signals suggesting successful infection (FIG. 4B).

Example 3

Figure 5:
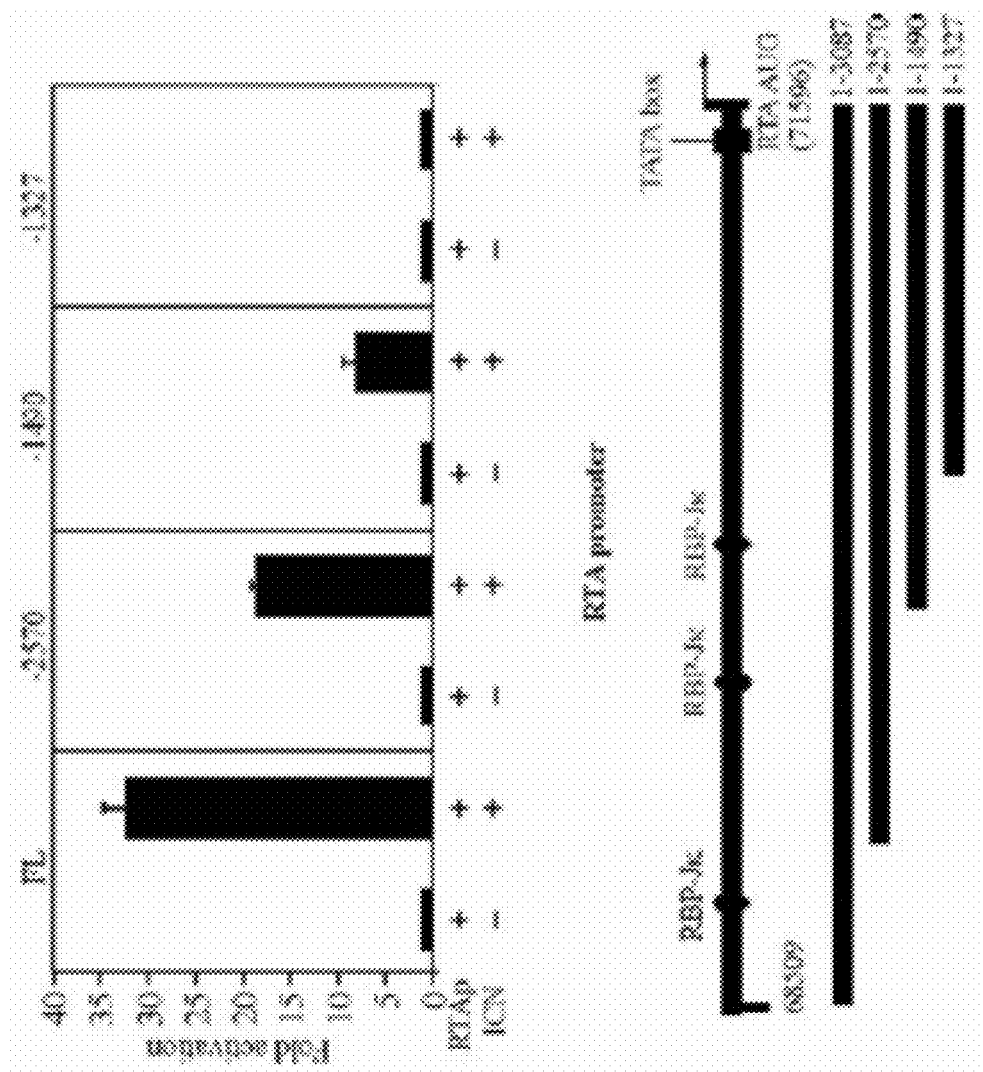
FIG. 5 shows transcriptional activity of ICN on RTA promoters. The reporter plasmid pRpluc contains a 3-kb sequence upstream of the translational initiation site of the RTA gene that drives the expression of firefly luciferase. A series of truncation promoters named as pRpluc. Δ 2570, pRpluc. Δ1490 and pRpluc. Δ 1327 were made for deletion of RBP-Jκ binding sites (bottom panel). A fixed amount (0.5 µg) of the reporter plasmids was transfected or co-transfected into U2OS cell with 50 ng of pflu-ICN. The promoter activity was expressed as the fold activation relative to the reporters alone control. The means and standard deviations from three independent transfections are shown.

RBP-Jκ Binding Sites within ORF50 Promoter are Critical for ICN-Mediated Regulation of RTA Expression To test if RBP-Jκ binding sites within RTA promoter are functional for ICN regulation, a series of truncated versions of the RTA promoter were employed (FIG. 5). In these truncated promoters, RBP-Jκ binding sites were removed sequentially until all RBP-Jκ binding sites were deleted to determine the contribution of each site to the regulation of RTA expression (FIG. 5). These reporter constructs were transfected into U2OS cells along with the expression vector pflu-ICN, an HA-tagged ICN expression vector. Activation of the promoter activity of more than 30-fold was observed when reporter constructs containing the full length (FL) RTA promoter with all the RBP-Jκ binding sites were co-transfected with the ICN expression vector (FIG. 5). However, this activation was not observed when co-transfections were performed with reporter construct pRplucΔ1327 deleted for most of the RBP-Jκ binding sites (FIG. 5). Interestingly, activation by ICN was gradually decreased when pRplucΔ2570 as well as pRplucΔ1490 sequentially deleted for RBP-Jκ binding sites were co-transfected with the ICN expression construct (FIG. 5). This indicated that each of the RBP-Jκ binding sites can contribute to the activation of the RTA promoter by ICN.

Example 4

Figure 6:
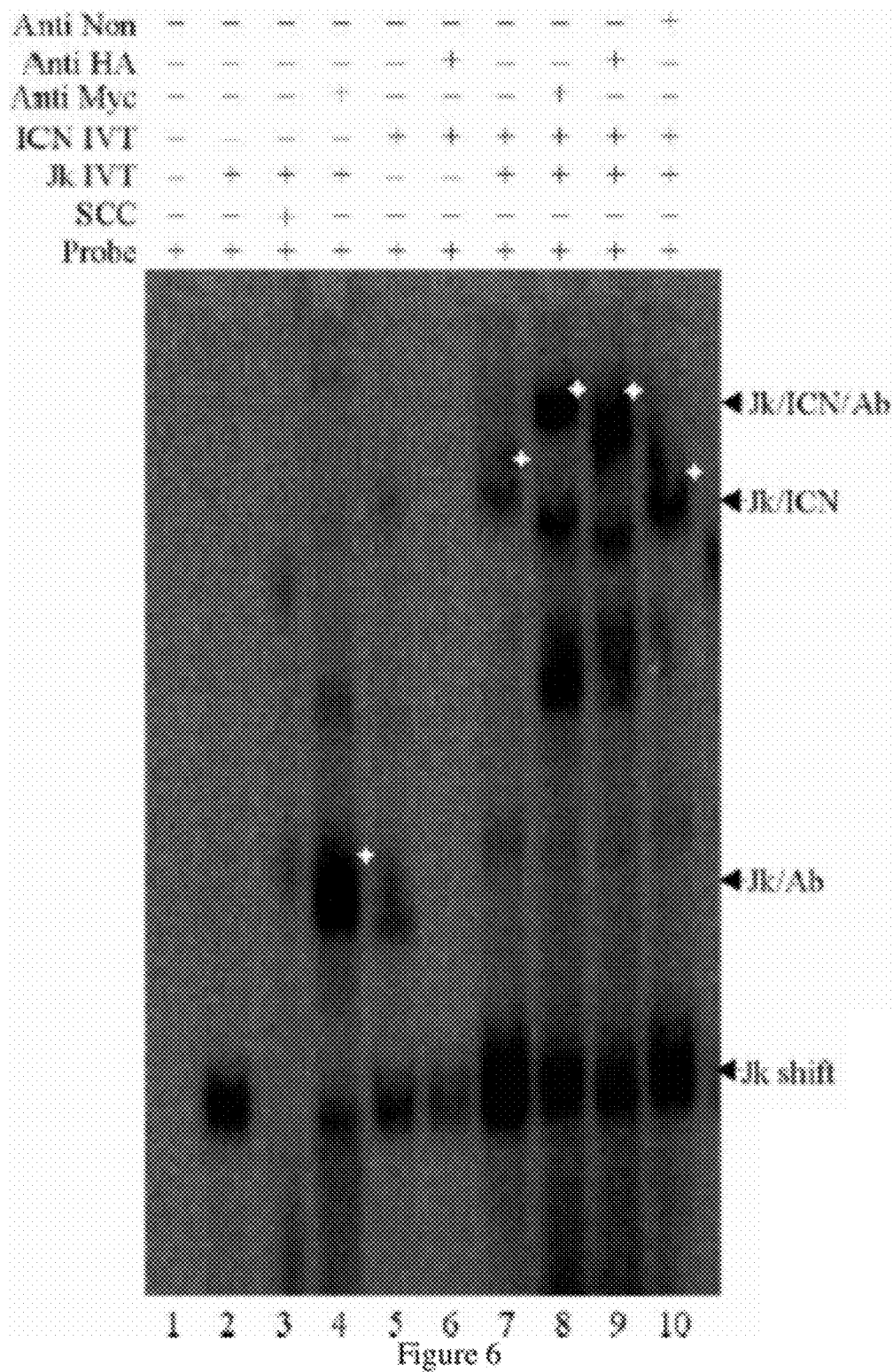
FIG. 6 shows ICN/RBP-Jκ DNA binding complex. The probe for the EMSA consists of an RBP-Jκ consensus binding sequence and the flanking bases from RTA promoter, the sequence of the probe is as follows: 5'-GATCATTTC-CGTGGGAAGACGAT-3' (SEQ ID NO. 3). RBP-Jκ/DNA complex is indicated. The asterisk indicates the position of the supershifted complex in the presence of ICN-HA and RBP-Jκ-myc in vitro translated mixture with specific antibodies. Non, nonspecific; IVT, in vitro translated; SCC, specific cold competitor.

RBP-Jκ Interaction with ICN Form Complexes Bound to its Cognate Sequence on the RTA Promoter In Vitro The results of the luciferase reporter assays above in Example ??? showed that the presence of potential RBP-Jκ binding sites within the RTA promoter is important for ICN's ability to activate the promoter. Therefore, to address whether ICN activates the RTA promoter through formation of an RBP-Jκ/ICN complex bound to the cis-acting DNA element within the RTA promoter, an electrophoretic mobility shift assay (EMSA) was performed. A probe was designed that contained the furthest downstream RBP-Jκ consensus binding sequence within the RTA promoter, as well as the 6 adjacent bases both 5' and 3' to the cognate sequence (Russo et al., 1996). The results of the EMSA assay show that a specific RBP-Jκ shift was observed with the probe in the presence of in vitro translated RBP-Jκ (FIG. 6, lane 2). The specificity of this band was demonstrated by its disappearance in the presence of specific competitor probe (FIG. 6, lane 3) and was further verified by its supershifting in the presence of specific antibody (FIG. 6, lane 4). In the presence of in vitro translated HA-tagged ICN, an additional shift was observed (asterisk, FIG. 6, lanes 7). This shift is likely to be formed by ICN/RBP-Jκ complex. The specificity of this band was further verified by its supershifting in the presence of specific antibodies (FIG. 6, lanes 8, 9), while no effect was observed in the presence of nonspecific antibody (FIG. 6, lane263 10). Data therefore indicate that RBP-Jκ form a complex with its consensus binding site within the RTA promoter and that ICN is able to associate with the complex of RBP-Jκ bound to its specific sequence.

Example 5

LANA Regulates Notch ICN Transactivation and Viral Reactivation

Figure 7:
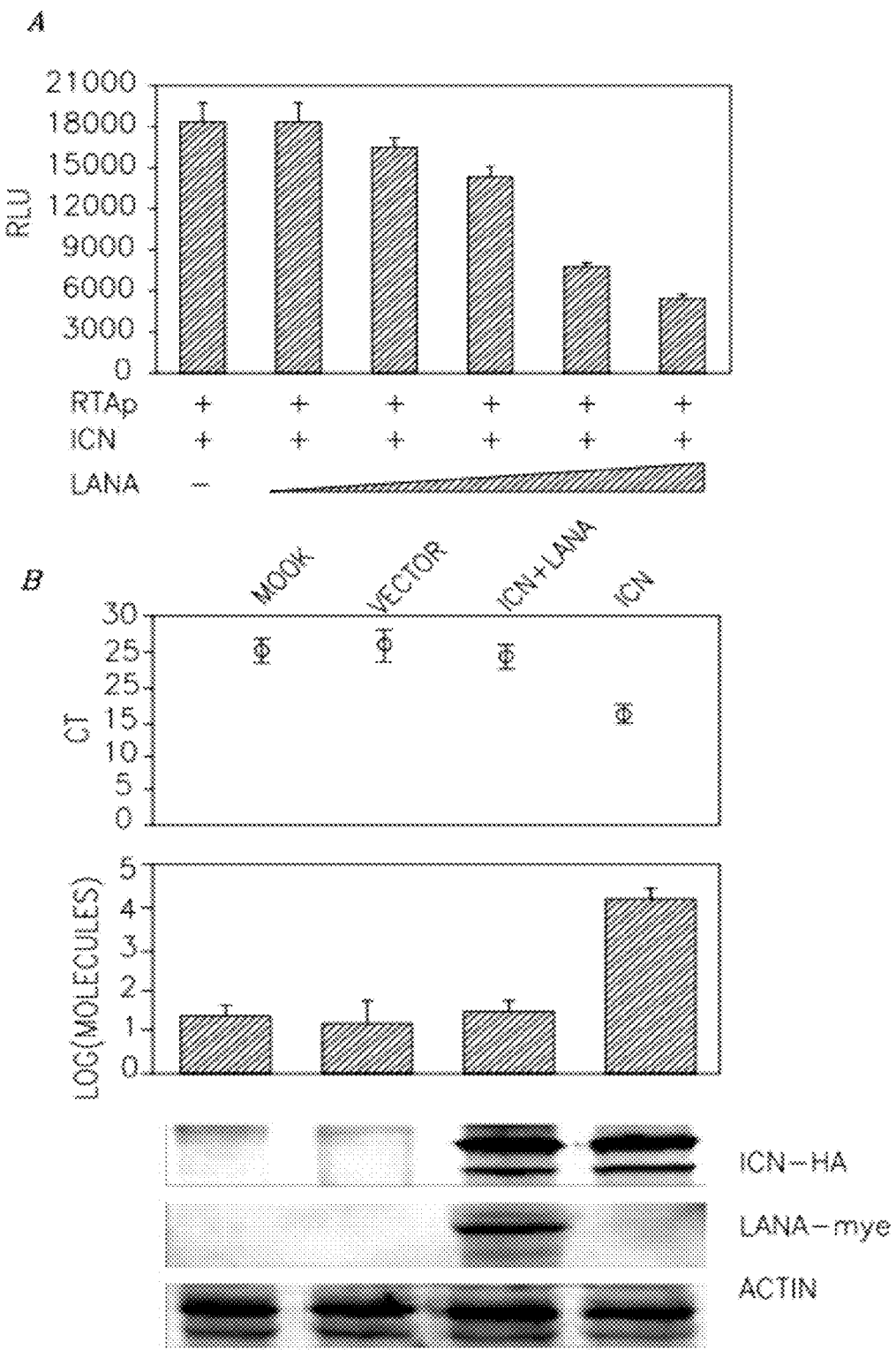
FIG. 7 shows (A) LANA represses ICN transactivation on RTA promoter. 1 million of U2OS cells were transfected with 0.5 ʎg RTA promoter reporter plasmid and 50 ng ICN expression vector along with increasing amount of LANA expression vector (0 ng, 10 ng, 20 ng, 50 ng, 100 ng, 200 ng) by lipofectamine 2000. Twenty four hours post-transfection, cells were harvested and lysed for reporter assay. (B) For each transfection, 15 million BCBL1 cells were transfected with mock, pA3M empty vector, and ICN with or without LANA. Twenty four hours post-transfection, total RNA was collected from the cells. A total of 5 ʎg of RNA was used with the Superscript First Strand Synthesis system to construct cDNA. Real-time PCR was performed using the DyNAmo SYBR Green qPCR kit with β-actin as the standard. The PCR data are expressed as the Ct values for RTA transcription. Each sample was tested in triplicate for the calculation of the mean and standard deviation. The relative transcript abundance (Log molecules) based on the Ct values for RTA. (C) Twenty million of Vero cells stably infected with Bac36 were mock-transfected or transfected with empty vector pA3M, ICN, or ICN plus LANA. Four days post-transfection, supernatant from each transfection was harvested and concentrated for infection of 293 cells. Twenty four hours post-infection, cells were harvested for FACS analysis to detect GFP expression marking the virus existence.
Figure 7:
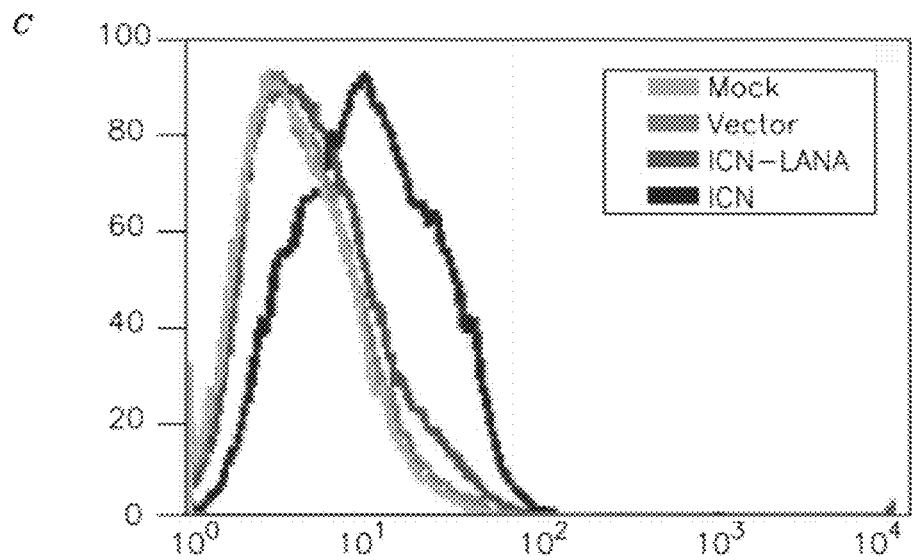

Although transfection experiments showed in Example 1 that ICN can drive lytic replication of KSHV, it is understandable that KSHV predominantly stays latent under physiological conditions in vivo and in vitro. This suggests that the accumulation of ICN in the majority of KSHV-positive cells has not crossed a threshold level which can overcome the latent state or there are built-in control mechanisms used by KSHV to antagonize the ability of ICN to reactivate the virus from latency. Additionally, LANA is predominantly expressed in all KSHV latently infected cells, and can maintain latency by down-regulating RTA expression. It is shown that LANA can also repress the ability of ICN to transactivate RTA expression and so maintain latency. Indeed, reporter assays showed that LANA can repress ICN transactivation of RTA in a dose-dependent manner (FIG. 7A). To determine if up-regulation of RTA by ICN can be shut down by LANA at the transcriptional level, real-time qPCR was performed to examine the effect on RTA expression in different transient transfection. BCBL1 cells were transfected with mock, empty vector, and ICN with or without LANA. BCBL1 cell line is latently infected with KSHV in which LANA expression level remains high to keep the virus in latent state. Total RNA was collected 24-h post-transfection for real-time PCR analysis. The results indicated that there was a higher Ct value in mock and vector-transfected BCBL1 cells which represents less copy number of RTA transcripts in these cells (FIG. 7B). However, Ct value for ICN-transfected BCBL1 was much lower, indicating accumulation of RTA transcripts in this sample (FIG. 7B). Ct value for ICN and LANA co-transfected BCBL1 was similar to mock and vector control. This shows that LANA is capable of shutting down RTA transcription by antagonizing ICN (FIG. 7B). Additionally, ICN expression levels were similar in both ICN-transfected and ICN/LANA co-transfected cells which indicated down-regulation of RTA is due to the presence of LANA but not due to the reduction of ICN (FIG. 7B). The Bac36 system was also took advantage of, to determine if exogenous expression of LANA could antagonize ICN by directly blocking the production of viral particles. Vero/Bac36 cells were transfected with ICN with or without LANA, similarly 4 days post-transfection, the supernatants of each transfection were collected and concentrated for infection of 293 cells. Twenty four hours post-infection, the cells were collected for FACS analysis. GFP signals were clearly detected in cells infected with supernatant from Vero/Bac36/ICN cells (FIG. 7C). However, there is little or no detectable levels of GFP found in cells infected with supernatant from Vero/Bac36 cells co-transfected with ICN and LANA similar to that seen for mock or vector (FIG. 7C). This indicates that LANA is capable of down-modulating the ability of ICN to reactivate KSHV and so 318 ensures maintenance of latency.

Example 6

Expression of Notch ICN is Up-Regulated in KSHV-Positive Cells

Figure 8:
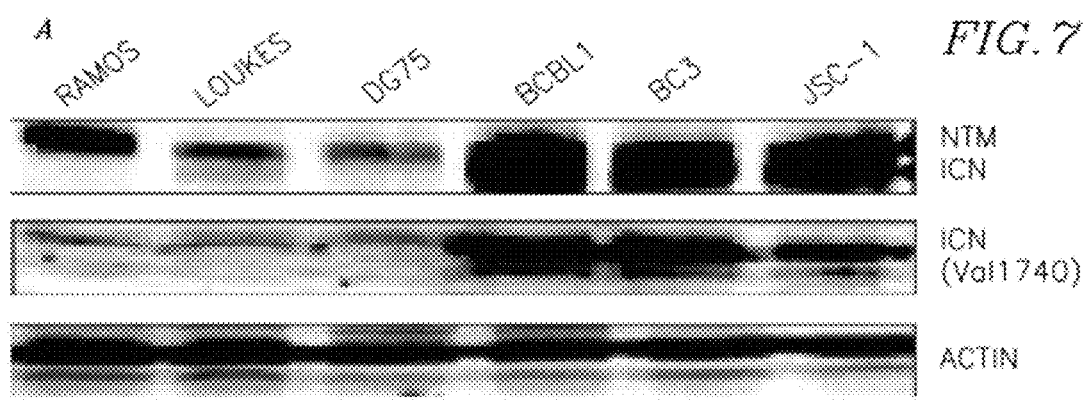
FIG. 8 shows Notch ICN is accumulated in KSHV-infected cells. (A) Western blot showing ICN levels in different cells. Cell lysates of Ramos, Loukes, DG75, BCBL1, BC3, and JSC1 cells were separated in an 8% sodium dodecyl sulfate-polyacrylamide gel, transferred to an NC membrane, and then blotted with anti-Notch rabbit serum. This antiserum recognizes the uncleaved transmembrane subunit NTM (upper band) and its intracellular cleavage product, ICN (bottom band). The same samples were also blotted with the Val1744 antibody, which specifically recognizes ICN. The loading amounts of lysates were normalized by the Bradford assay. Quantification of the relative density (RD) of ICN in each cell is also shown. (B and C) Cells were fixed and stained with anti-LANA human serum or the Val1744 rabbit polyclonal antibody, which specifically recognizes ICN. Staining was visualized with goat anti-human-fluorescein isothiocyanate or goat anti-rabbit-Texas Red antibodies.
Figure 8:
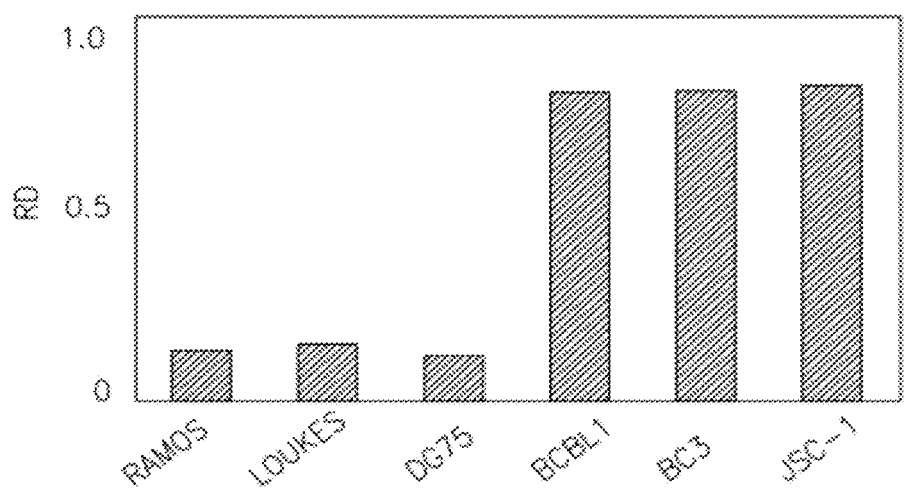
Figure 8:
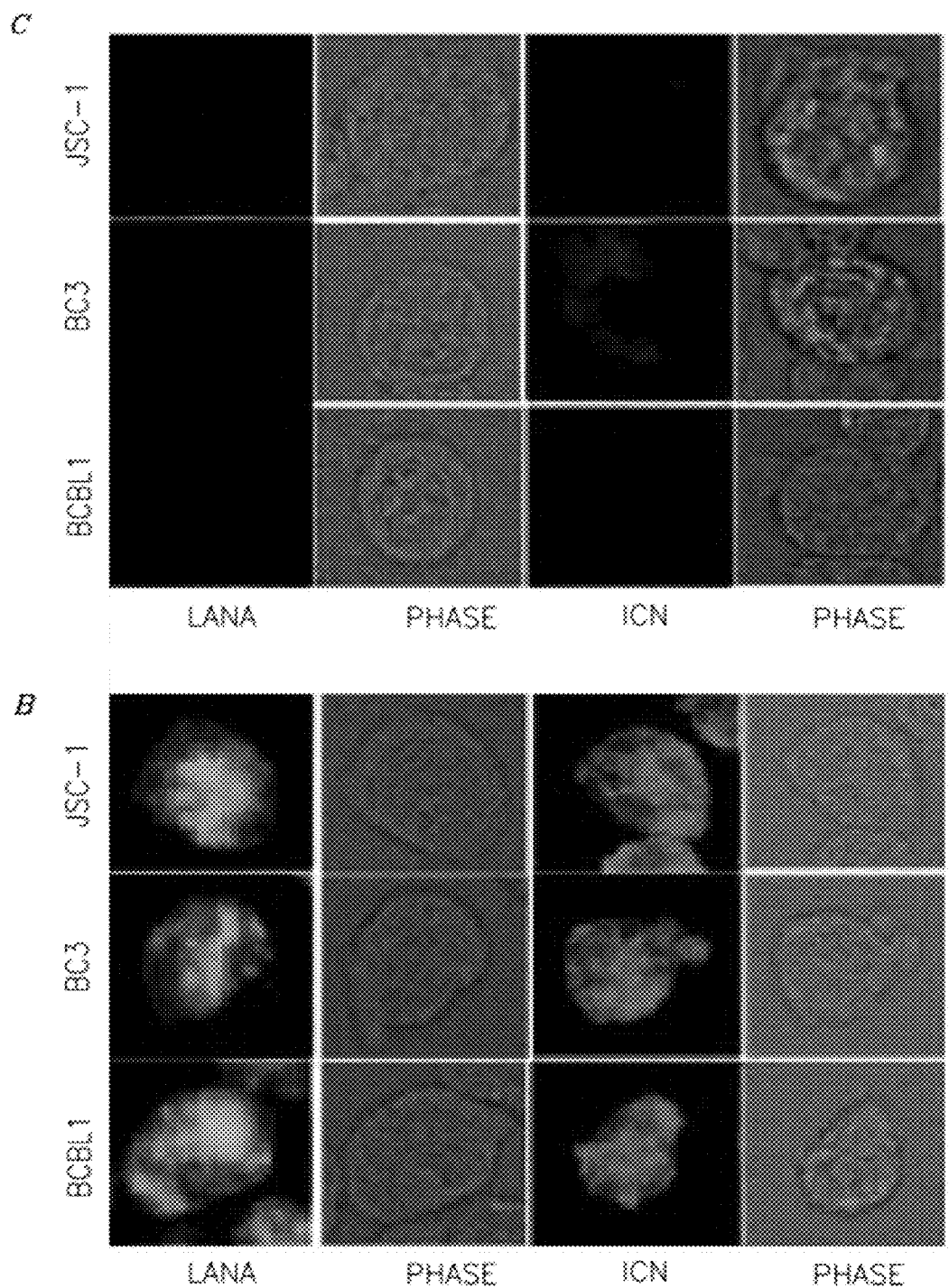

It was desirable to explore the expression levels of ICN in KSHV-infected PEL cells, as ICN may also have an impact on KSHV in terms of regulation of the viral life cycle or on KSHV-mediated pathogenesis in the virus-host environment. To determine the expression of ICN in KSHV-infected PELs, Western blot analysis of the PEL cell lines BCBL1, BC3, and JSC1, which are all latently infected with KSHV, was performed. The results showed dramatically elevated levels of ICN in KSHV-positive PEL cells compared to those in the KSHV-negative B-lymphoma cell lines Ramos, Loukes, and DG75 based on signals from the ICN-specific antibody Val1744 (FIG. 8A). These findings were further corroborated by immunostaining of ICN in these cells. LANA was typically expressed in the nuclei of all KSHV-positive cells, with a characteristic punctate pattern which indicates the existence of the virus (FIG. 8B, upper panels), but there were no detectable levels of LANA in KSHV-negative cells (FIG. 8C, upper panels). Interestingly, ICN was strongly positive in KSHV-infected PEL cells (FIG. 8B, bottom panels) compared to the weak ICN signals in KSHV-negative B-cell lines (FIG. 8C, bottom panels).

Example 7

Accumulation of Notch ICN is Correlated with KSHV Infection and LANA Expression

Figure 9:
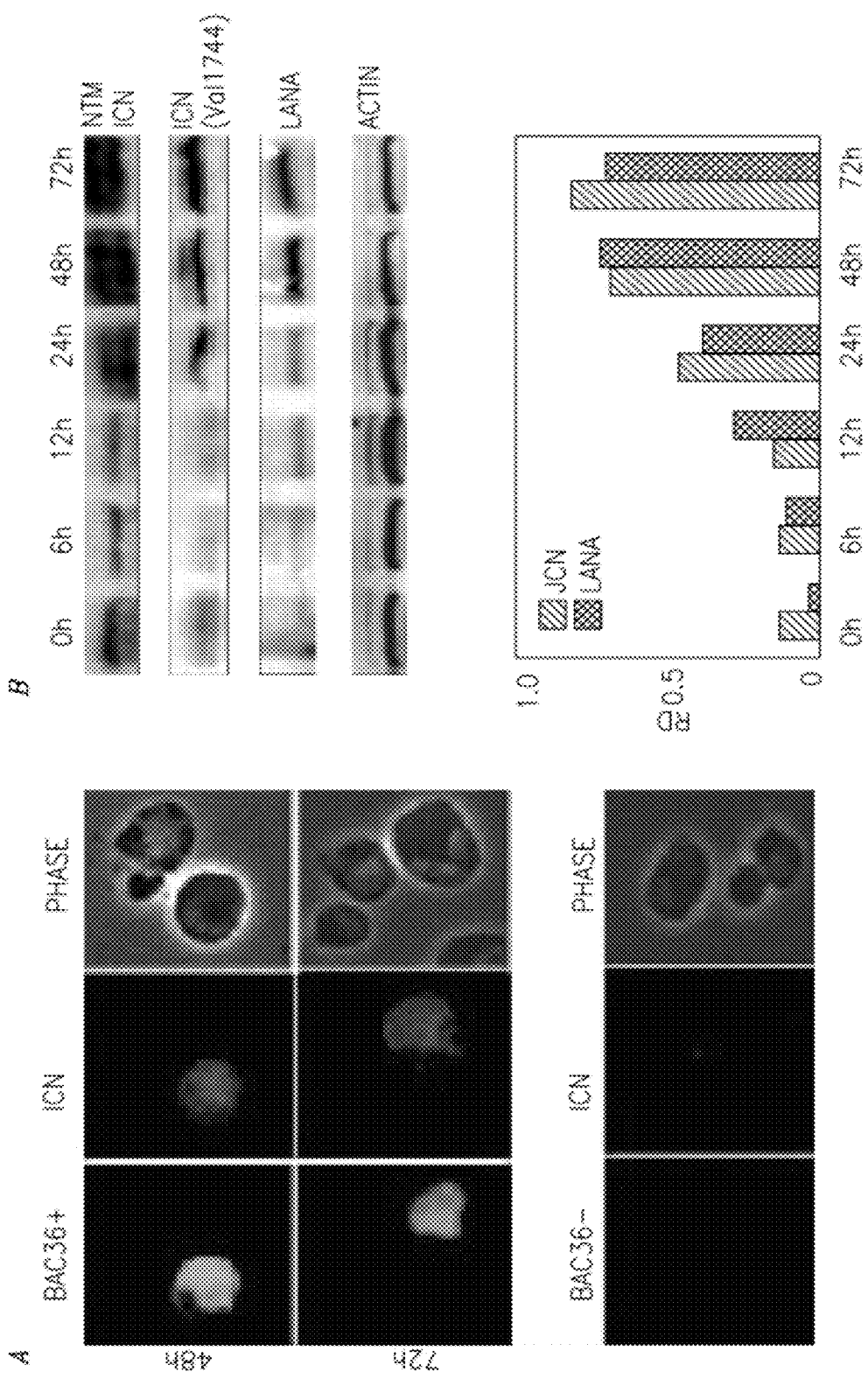
FIG. 9 shows (A) ICN is accumulating in de novo KSHV-infected cells. Twenty million Vero cells stably infected with the Bac36 KSHV-GFP recombinant virus were induced with tetradecanoyl phorbol acetate (20 ng/ml) and sodium butyrate (1.5 mM) for 4 days, and then the supernatant was filtered with a 0.45-_m filter and concentrated for each infection of 293 cells. At 48 h or 72 h postinfection, cells were fixed and stained with Val1744 antibody. Staining was visualized with goat anti-rabbit-Texas Red antibody. Virus existence was determined by the GFP marker. (B) ICN is up-regulated in KSHV-challenged cells. For each infection, 50 million BCBL1 cells were induced with tetradecanoyl phorbol acetate and sodium butyrate as described above. The supernatant was filtered with a 0.45-_m filter and concentrated by centrifugation at 18,000 rpm for 2 h; the virion pellet was resuspended in 100 _l PBS for inoculation of 293 cells. Cells were harvested at different times postinfection, and cell lysates were made for Western blot analysis. The relative densities (RD) of ICN and LANA in each cell treated with virus are also shown.

The data in Example 6 demonstrated that ICN is highly expressed in KSHV-positive cells compared to KSHV-negative cells of the same B-cell origin. However, these results did not determine if the accumulation of ICN in KSHV positive cells was due to KSHV infection. To determine if KSHV infection mediates ICN accumulation, 293 cells were infected with Bac36, a recombinant KSHV expressing GFP which enables monitoring of viral infection. Bac36 has a similar gene expression profile to that of wild-type KSHV. By using Bac36, it is easy to compare gene expression levels between KSHV-positive (infected) and -negative (uninfected) cells within the same isogenic background of the cell culture system. At 24 h post infection, GFP signals were observed, followed by preparation of the cells for immunofluorescence analysis. Immunostaining showed strong ICN signals in KSHV infected, GFP-positive cells. As expected, low levels of ICN were observed in GFP-negative, uninfected cells (FIG. 9A). To further support these studies, we also harvested 293 cells infected with KSHV virions induced from BCBL1 at different time points to determine the levels of ICN. The results of Western blot analysis indicated that ICN began to accumulate at 24 h post infection (FIG. 9B), the time at which KSHV typically establishes latency after infection and at which LANA's expression reaches a consistently high level.

Example 8

LANA Expression is Critical for Accumulation of ICN in Human B Cells

Figure 10:
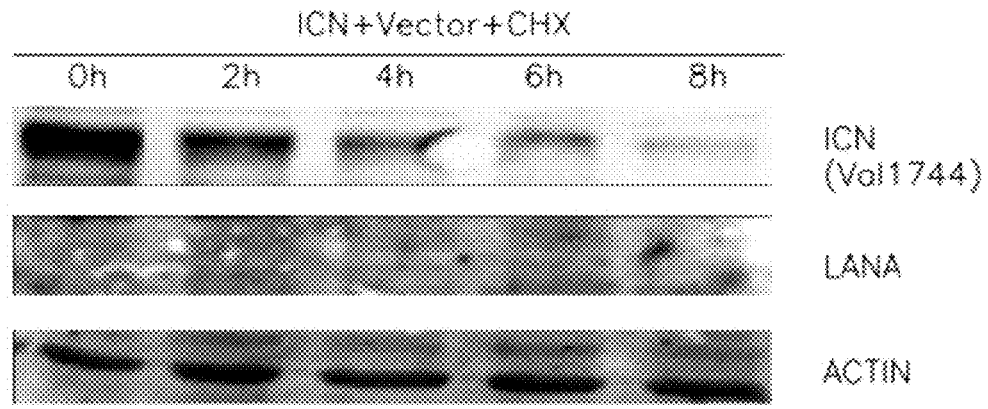
FIG. 10 shows LANA stabilizes ICN. For each transfection, 15 million DG75 cells were transfected with 10 μg ICN without (A) or with (B) 10 _g LANA. At 24 h post transfection, cells were treated with cycloheximide at 100 μg/ml. At 0 h, 2 h, 4 h, 6 h, and 8 h post treatment, cells were harvested for Western blot analysis. The relative density (RD) of ICN in each sample is also shown (C).
Figure 10:
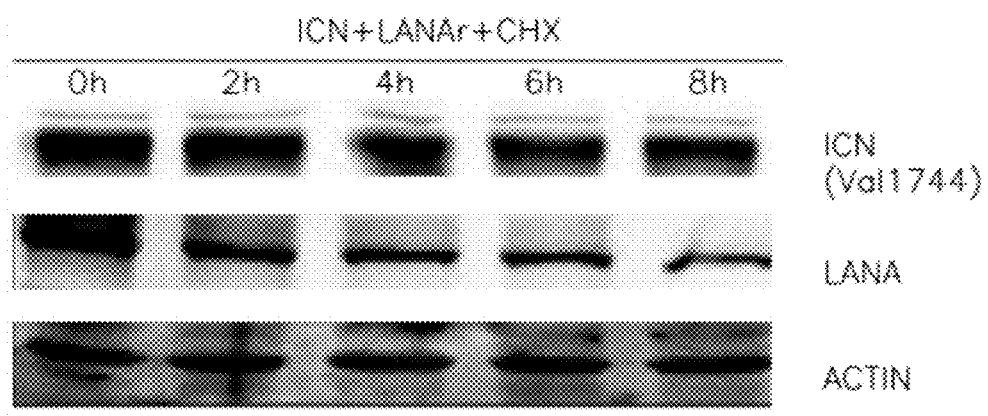
Figure 10:
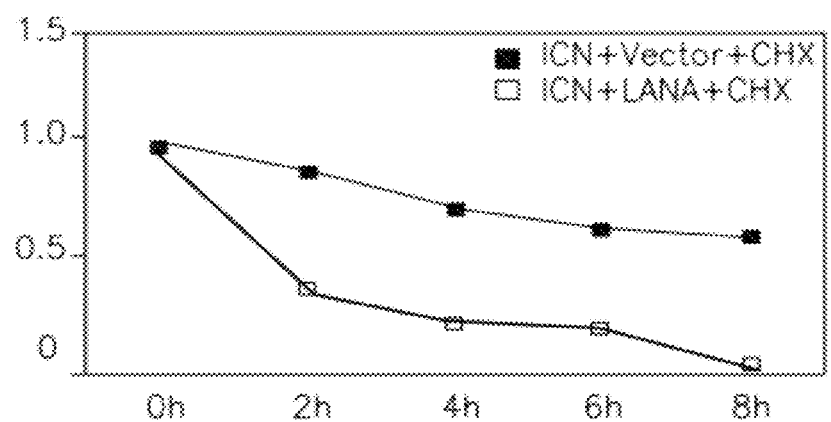

To address the potential mechanisms for ICN accumulation in KSHV-infected cells, real-time PCR was employed to determine the transcription levels of Notch1 in different cell lines; however, the mRNA levels of Notch1 were similar in both KSHV-positive and -negative cells. This indicates that ICN accumulation is likely mediated by a posttranslational mechanism. Additionally, our data in Examples 1,2 and 6-7 demonstrated that ICN levels correlated with establishment of viral latency. Since LANA is predominantly expressed in latently KSHV-infected cells, LANA was chose as the target and hypothesis was made that LANA may be responsible for ICN accumulation. DG75 cells were transfected with the ICN expression vector, with or without LANA, followed by cyclo-heximide treatment at 24 h posttransfection to inhibit new protein synthesis. By 2 h posttreatment, the ICN level was rapidly decreased in control cells and was barely detectable by 8 h (FIG. 10A). However, in the presence of LANA, ICN levels remained relatively constant for 8 h (FIG. 10B). These results strongly suggest that LANA can play a prominent role in regulating ICN stability and degradation.

Example 9

Figure 11:
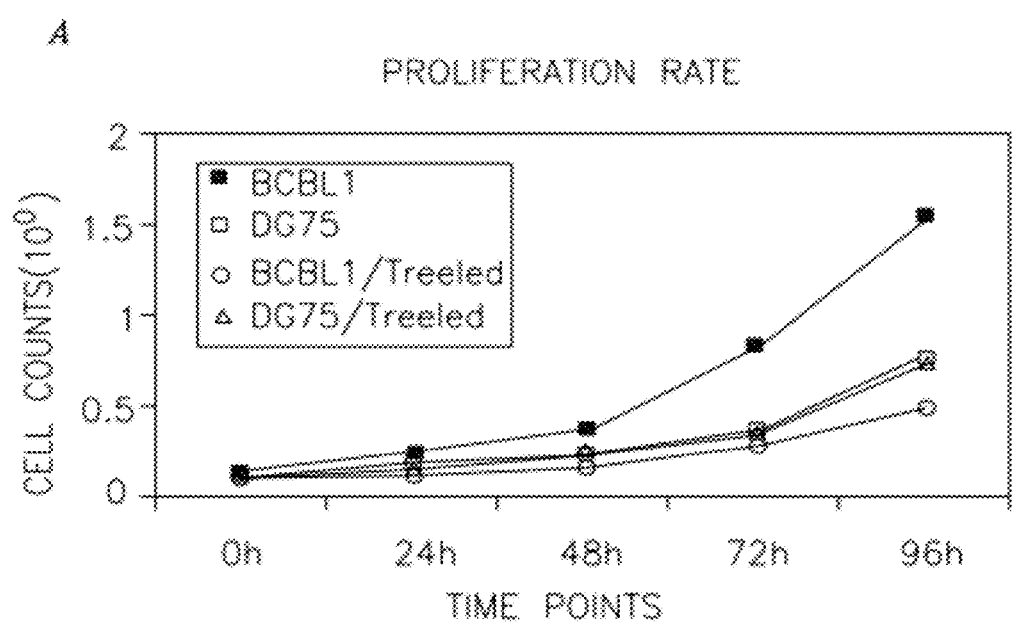
FIG. 11 shows (A) Comparison of proliferation rates of cells. Each cell type (100,000 cells) was cultured in RPMI 1640 with 5% BGS. At each time point, cells were stained with trypan blue and counted. The results represent three independent experiments. (B) CFSE staining showing mitosis of DG75 (left panel) and BCBL1 (right panel) cells. Five million cells were cultured in RPMI 1640 with 5% BGS and mock treated (red curves) or treated with γ-secretase inhibitor at 20 μM (blue curves). At 48 h post treatment, cells were harvested for FACS analysis to determine mitotic activity. Gray and black curves represent negative and positive controls, respectively. The negative control was non-CFSE-staining cells, and the positive control was CFSE-staining but immediately fixed cells. (C) 7AAD staining analysis of mock treated (left panel) and KSHV-infected (right panel) primary B cells. Two million primary B cells were mock treated or KSHV infected for 4 weeks and harvested for 7AAD staining. The percentages of dead and necrotic cells are shown. (D) Four-week KSHV-infected primary B cells were harvested and mock treated (left panel) or treated with γ-secretase inhibitor (right panel) for 5 days, and then cells were stained with 7AAD for FACS analysis.
Figure 11:
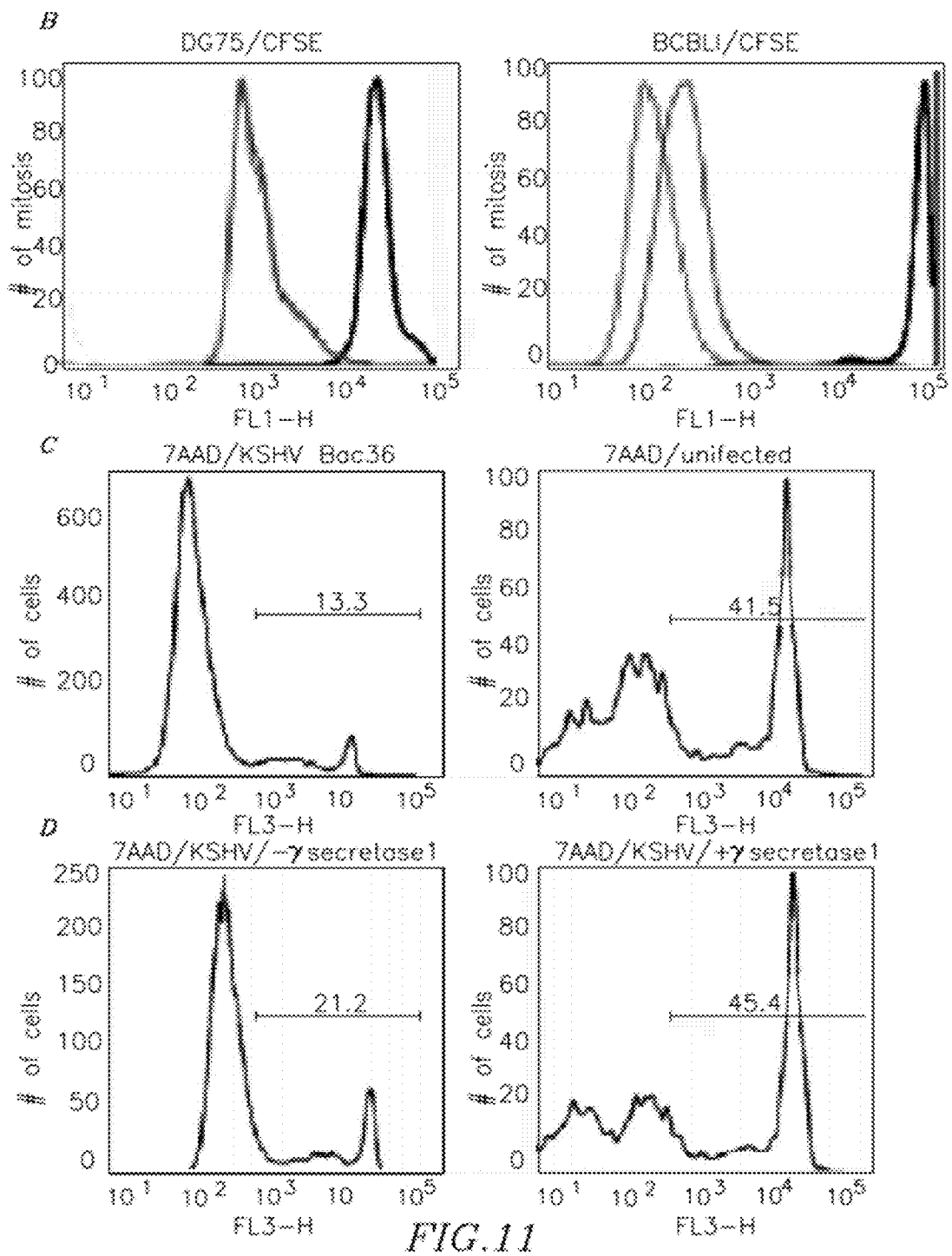

Accumulation of Notch ICN Results in Increased Cellular Proliferation and Plays a Critical Role in KSHV-Mediated Transformation As was mentioned previously, aberrant Notch signaling is highly associated with oncogenesis. To determine the functional consequences associated with the accumulation of ICN in KSHV-infected cells, the rate of proliferation of KSHV-infected B cells in which ICN levels remained high was compared to that of control KSHV-negative B cells with lower ICN expression levels. The results demonstrated that the rate of proliferation of the KSHV-infected BCBL1 cells was statistically higher than that of the KSHV-negative DG75 cells (FIG. 4A). Furthermore, a γ-secretase inhibitor which can block the production of ICN dramatically slowed the proliferation of BCBL1 cells, with the proliferation of DG75 cells being minimally affected by the γ-secretase inhibitor (FIG. 11A). This was most likely due to the increased levels of ICN in the infected cells. These results were further corroborated by studies examining mitotic activity by using CFSE staining. CFSE labels cell membranes, and the signal is proportionally lost with each generation producing new daughter cells. Cells stained with CFSE followed by treatment with the γ-secretase inhibitor for 48 h were monitored by FACS. In BCBL1 cells the mitotic activity was dramatically decreased compared to that in untreated cells (FIG. 11B, right panel). A similar effect was also observed in JSC1 cells, which are dually infected with KSHV and EBV, but with KSHV gene expression being predominant. However, the mitotic activities of treated and untreated DG75 cells were relatively unchanged (FIG. 11B, left panel).

In this Example, it was desired to determine if aberrant Notch signaling plays a role in KSHV prolonging the lifespan of endothelial cells. Thus, primary B lymphocytes were infected with the KSHV recombinant Bac36. Proliferating lymphocytes were seen by 4 weeks after infection with KSHV Bac36. However, uninfected control cells did not survive, with most cells being dead by 30 days in culture under the same conditions. FACS analysis with 7AAD staining showed that only 13.3% of cells from the Bac36-infected population showed positive staining indicating death (FIG. 11C, left panel). In the uninfected population, about 41.5% of the cells were dead, with the remainder of the population being mixed with cell debris (FIG. 11C, right panel). Interestingly, when the 4-week-infected B cells were treated with γ-secretase inhibitor for 5 days, analysis by FACS showed that about 45.4% of cells had undergone death (FIG. 11D, right panel), in contrast to 21.2% of the mock-treated cells (FIG. 11D, left panel). These findings strongly suggest that KSHV prolongs the life-span of B cells, as evidenced by a 70% reduction in dead cell levels. These results indicate that ICN can contribute to the survival of KSHV-infected cells. In addition, it was noticed that in the Bac36-infected group, a portion of cells were GFP positive, indicating the presence of the virus within the B cells or lymphoblastoid cells. This suggests that ICN accumulation within these cells may up-regulate cellular cytokines, supporting the growth of uninfected cells in the population through a paracrine mechanism.

Example 10

Inactivation of Notch1 Cleavage by γ-Secretase Inhibitor is Responsible for G1 Arrest in KSHV-Infected Cells As was shown in the above Examples; a γ-secretase inhibitor can dramatically slow down proliferation of the KSHV-positive BCBL1 cell line. This Examples demonstrates the possible mechanism for this decrease of the proliferating rate caused by the γ-secretase inhibitor. Cell cycle analysis of these cells showed that approximately 30% more γ-secretase inhibitor-treated BCBL1 cells than mock-treated BCBL1 cells were arrested at G1 phase of the cell cycle (FIG. 12A). In contrast, there were no significant changes in G1 phase of the DG75 cell cycle when these cells were treated with γ-secretase inhibitor (FIG. 12B). Moreover, Western blotting showed that ICN levels were decreased in BCBL1 cells treated with γ-secretase inhibitor (FIG. 12A). In contrast, the control DG75 cells showed similar cell cycle patterns for mock-treated cells and those treated with γ-secretase inhibitor. Additionally, Western blot analysis demonstrated that the uncleaved transmembrane form of Notch1 was the predominant signal in these cells (FIG. 12B). These results indicate that there was no active cleavage of Notch1 to the activated intracellular form in DG75 cells and explain why the γ-secretase inhibitor was ineffective in regulation of cell proliferation of this KSHV-negative cell line.

Example 11

Accumulation of Notch ICN Up-Regulates Cyclin D1

Figure 13:
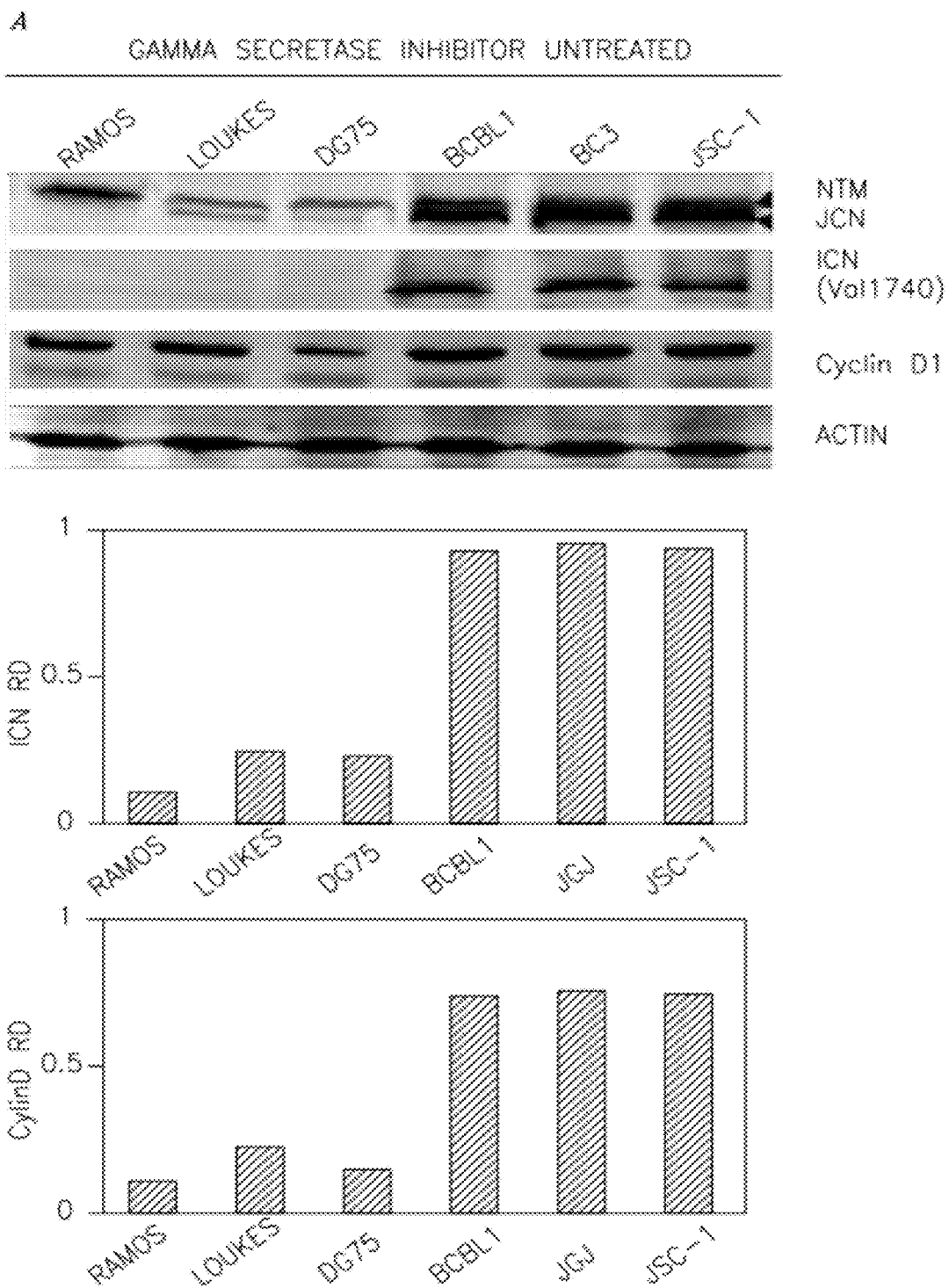
FIG. 13 shows (A) Western blot showing levels of NTM and ICN forms of Notch1 in different cells. The same membrane was stripped and probed for cyclin D1. (B) Western blot showing levels of NTM and ICN forms of Notch or cyclin D1 in _-secretase inhibitor-treated cells. In both cases, the Val1744 antibody was used to confirm the presence of ICN. Quantification of the relative density (RD) of ICN or cyclin D1 is also shown.
Figure 13:
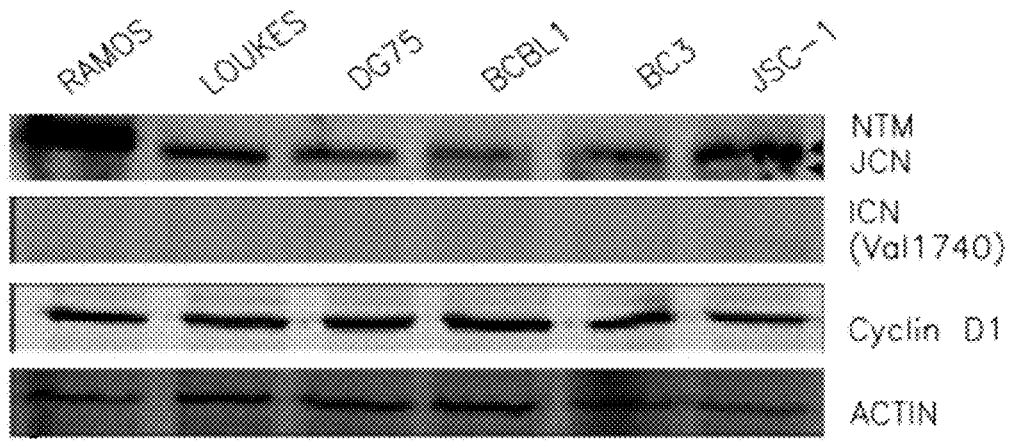
Figure 13:
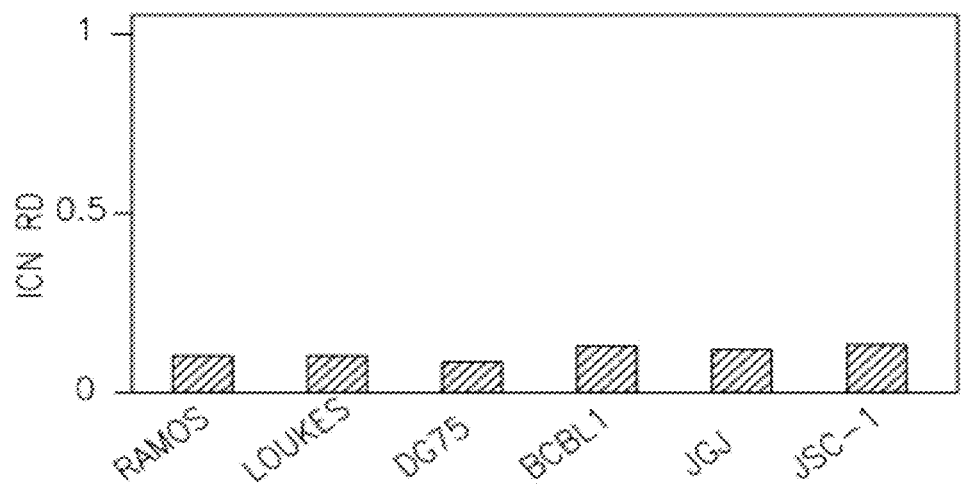
Figure 13:
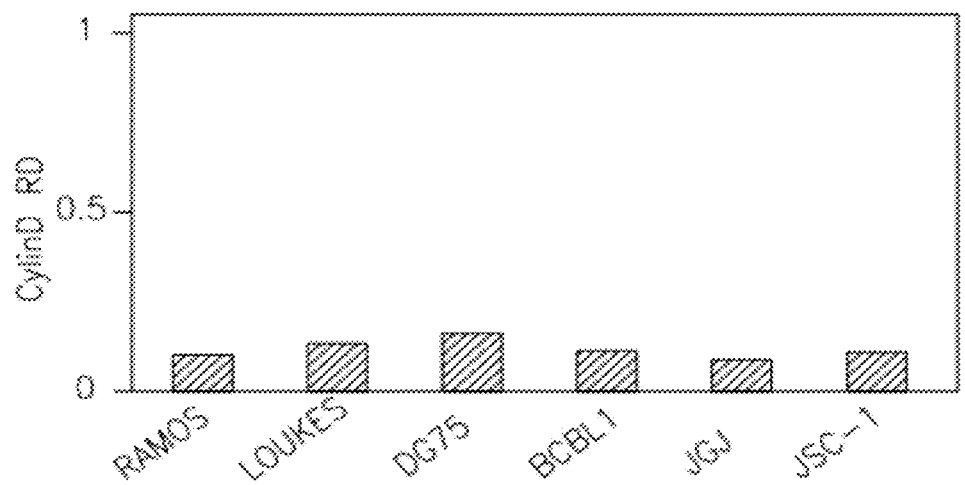

Cyclin D1, a subunit of the cyclin D1/CDK2 complex, phosphorylates and inactivates the retinoblastoma protein and thus promotes progression through the G1/S phase of the cell cycle. In the above Examples, it was shown that KSHV-positive cells treated with the γ-secretase inhibitor were arrested at the G1 phase. This indicates that elevated levels of ICN in these cells may have a role in regulation of cyclin D1. To determine if the increased levels of ICN in KSHV-infected cells led to any change in cyclin D1 levels, we screened KSHV infected cells by Western blotting. The results demonstrated that the expression level of cyclin D1 was at least twofold higher in KSHV-infected cells than in KSHV-negative cells (FIG. 13A), with the relative density signals indicating that this could be much more and may be as high as fourfold (FIG. 13A, lower panel). Interestingly, this increase in cyclin D1 levels was a specific response to ICN levels, as cyclin D1 levels were depressed when KSHV-positive cells were treated with γ-secretase inhibitor, which blocked ICN production (FIG. 13B). Luciferase assays also indicated that the cyclin D1 promoter is responsive to ICN (FIG. 14A). Additionally, forced expression of ICN from a heterologous promoter which is not dependent on cleavage to process Notch1 to ICN in γ-secretase inhibitor treated BCBL1 cells partially recovered the expression level of cyclin D1 (FIG. 7B). These findings strongly support the hypothesis that KSHV infection leads to an increase in ICN, stimulating proliferation of the infected cells. This effect was reversed when the cells were treated with a γ-secretase inhibitor, as shown by a reduced proliferation rate and arrest in G1 phase.

Example 12

Figure 16:
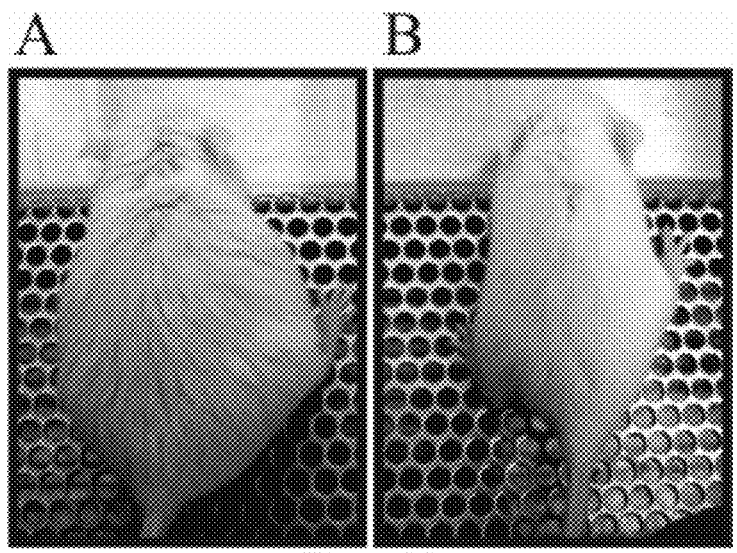
FIG. 16 shows: GSI slows down the growth of KSHV infected B lymphoma cells in vivo. Representative control (A) and GSI treated (B) mouse is shown. 10 million BCBL1 cells were inoculated first in the SCID mice which is susceptible for BCBL1 cell growth through intraperitoneal injection; then 30 mg/kg GSI (treated group) or Saline (Mock treated) was injected intraperitoneally daily. Tumors and acites rapidly formed in mock treated mouse and however the formation of tumor and acites in GSI treated mice is greatly delayed.
Figure 17:
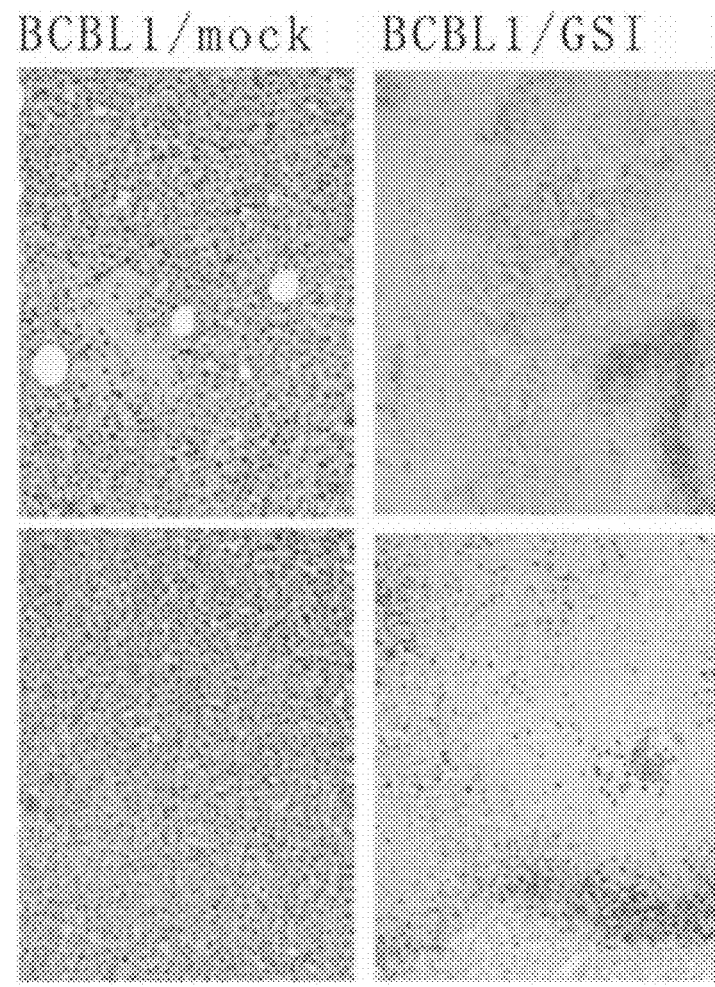
FIG. 17 shows: GSI results in necrosis and apoptosis of BCBL1 cells in vivo. The left panel shows that there is no cytopathic effect in mock treated BCBL1 cells and there are a lot of necrotic and apoptotic cells among the GSI treated BCBL1 cells in right panel.
Figure 18:
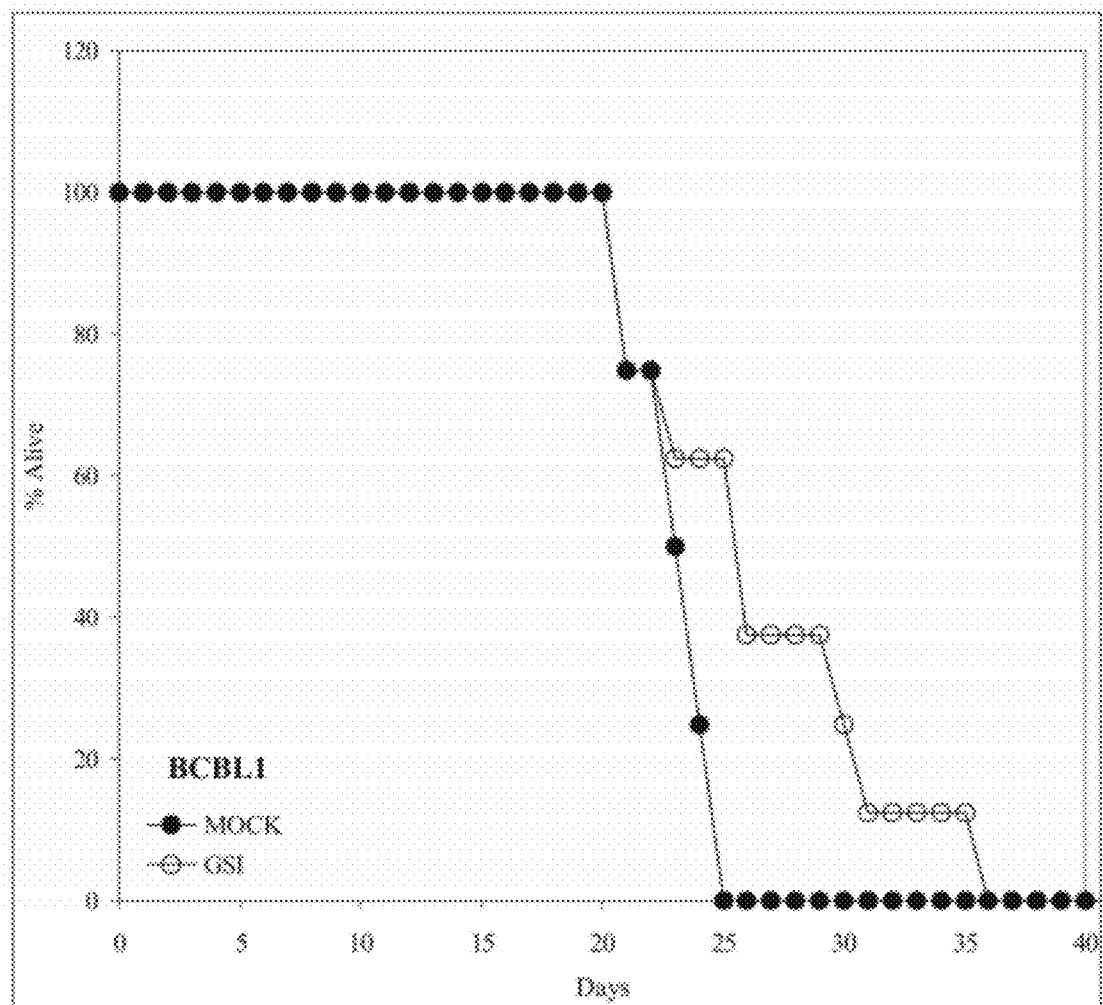
FIG. 18 shows the survival time curve of Control and GSI treated mice. GSI can significantly increase the survive time of treated mice.

Gamm Secretase Inhibitor Adversely Affects Proliferation of KSHV Infected B Lymphoma Cells As shown in the previous examples, gamma-secretase inhibitor (GSI) which specifically blocks the production of ICN in cells can inhibit the proliferation of KSHV infected B lymphoma cells in vitro. This indicates that GSI has potential therapeutic value for the management of KSHV infected B lymphoma patient. To confirm the results, a test was carried out to see if GSI can affect the proliferation of KSHV positive B lymphoma cells in vivo. An animal model was first established by using SCID mouse which is susceptible for the growth of KSHV infected B lymphoma cell line BCBL1. And then we used GSI to treat the mouse daily at dose 30 mg/kg and used saline as a control. In this study, it was found that GSI can greatly slow down the progression of the tumor in vivo (FIG. 16), in addition, GSI was found to significantly prolong the survival time of the mice treated with GSI compared to the control mice (FIG. 17). Tumor tissue samples were collected from the GSI treated and mock treated mouse and a histopathological study was done to look for the changes of the tumor cells caused by GSI. GSI was found to cause necrosis and apoptosis of the BCBL1 cells from the treated mouse (FIG. 18). In contrast, there are relatively no changes of BCBL1 cells from the saline mock treated mouse (FIG. 18). These results demonstrate that GSI can antagonize the growth of KSHV infected B lymphoma cells in vitro and in vivo and prove the potential therapeutic value of this small compound for KSHV induced tumors.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method for treating a virus-induced lymphoproliferative disease, the method, comprising: the step of administering to a subject in need thereof a therapeutically effective amount of a γ-secretase inhibitor.

2. The method of claim 1, wherein the virus is an Epstein-Barr virus (EBV) or a human herpesvirus 8 (HHV8).

3. The method of claim 1, wherein the virus is a γ-herpesvirus.

4. The method of claim 3, wherein the virus-induced lymphoproliferative disease is γ-herpesvirus-related B lymphoma.

5. The method of claim 4, wherein the γ herpesvirus-related B lymphoma is primary effusion lymphoma (PEL), multicentric Castleman's disease (MCD), Epstein-Barr virus (EBV) transformed lymphoma or a combination thereof.

6. The method of claim 1, wherein the γ-secretase inhibitor is N-[N-(3,5-difluorophenacetyl)-L-alanyl]-(S)-phenylglycine t-butyl ester (DAPT), L-852,505, L-685,458, 2-[(1R)-1-[[(4-chlorophenyesulfony](2,5-difluorophenyl)amino] ethyl]-5-fluoro-benzenepropanoic acid (BMS-299897), or a combination thereof.

7. The method of claim 1, further comprising the step of administering to the subject an agent capable reducing expression or function of latency associated nuclear antigen (LANA), cyclin D1 or their combination.

8. The method of claim 7, wherein reducing expression or function of latency associated nuclear antigen (LANA), cyclin D1 or their combination, comprises lowering the level of a protein or nucleic acid regulating the expression or function of said latency associated nuclear antigen (LANA), cyclin D1 or their combination.

9. The method of claim 7, wherein said agent is a siRNA, a virus, polyamides, triple-helix-forming agents, antisense RNA, synthetic peptide nucleic acids (PNAs), agRNA, LNA/DNA copolymers, or a combination thereof.

10. The method of claim 1, wherein treating comprises preventing, inhibiting or suppressing symptoms associated with said lymphoproliferative disease.

11. The method of claim 1, wherein treating comprises: ameliorating symptoms, reducing symptoms, delaying onset of said lymphoproliferative disease, or a combination thereof.

12. A method of inhibiting or suppressing production of intracellular Notch1 (ICN) resulting from viral infection, comprising contacting an infected host cell with an effective amount of a γ-secretase inhibitor, wherein said γ-secretase inhibitor arrests growth of the infected host at the G1 phase.

13. The method of claim 12, wherein the infecting virus is an Epstein-Barr virus (EBV) or a human herpesvirus 8 (HHV8).

14. The method of claim 12, wherein the infecting virus is a γ-herpesvirus.

15. The method of claim 12, wherein the γ-secretase inhibitor is N-[N-(3,5-difluorophenacetyl)-L-alanyl]-(S)-phenylglycine t-butyl ester (DAPT), L-852,505, L-685,458, 2-[(1R)-1-[[(4-chlorophenyesulfony](2,5-difluorophenyl)amino] ethyl]-5-fluorobenzenepropanoic acid (BMS-299897), or a combination thereof.

* * * * *

UNITED STATES PATENT AND TRADEMARK OFFICE
CERTIFICATE OF CORRECTION

PATENT NO. : 8,957,012 B2
APPLICATION NO. : 13/357452
DATED : February 17, 2015
INVENTOR(S) : Robertson et al.

It is certified that error appears in the above-identified patent and that said Letters Patent is hereby corrected as shown below:

In the Specification

Please replace Column 1, Lines 15-20 with the following paragraph:
This invention was made with government support under CA091792, CA072150, and DE001436 awarded by the National Institutes of Health. The government has certain rights in the invention.

Signed and Sealed this
Twenty-fifth Day of April, 2023

Katherine Kelly Vidal
*Director of the United States Patent and Trademark Office*